United States Patent [19]

Rainer

[11] Patent Number: 4,555,518

[45] Date of Patent: Nov. 26, 1985

[54] FLUOROALKOXY SUBSTITUTED BENZIMIDAZOLES USEFUL AS GASTRIC ACID SECRETION INHIBITORS

[75] Inventor: Georg Rainer, Konstanz, Fed. Rep. of Germany

[73] Assignee: Byk Gulden Lomberg Chemische Fabrik GmbH, Konstanz, Fed. Rep. of Germany

[21] Appl. No.: 606,872

[22] Filed: May 1, 1984

[30] Foreign Application Priority Data

May 3, 1983 [CH] Switzerland ................ 2401/83

[51] Int. Cl.[4] ................ C07D 403/12; A61K 31/44
[52] U.S. Cl. ................ 514/338; 546/271
[58] Field of Search ................ 424/263; 546/271

[56] References Cited

U.S. PATENT DOCUMENTS

| 4,045,563 | 8/1977 | Berntsson et al. ............ 546/271 |
| 4,045,564 | 8/1977 | Berntsson et al. ............ 546/271 |
| 4,337,257 | 6/1982 | Janggren et al. ............ 546/271 |

FOREIGN PATENT DOCUMENTS 0045200 2/1982 European Pat. Off. ............ 546/271

OTHER PUBLICATIONS

Yale, J. Med. and Pharm. Chemistry, vol. 1, No. 2, 1959, p. 131.
Pinder et al., J. of Pharm. Sci., vol. 56, No. 8, 1967, 970–971.

Primary Examiner—Jane T. Fan
Attorney, Agent, or Firm—Berman, Aisenberg & Platt

[57] ABSTRACT

Fluoroalkoxy compounds of the general formula I

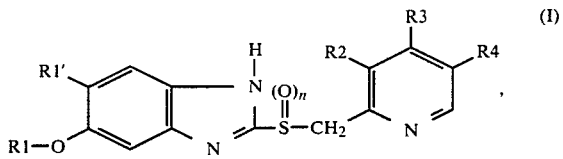

wherein R1 represents a 1–3C-alkyl radical which is completely or predominantly substituted by fluorine, or a chlorodifluoromethyl radical, R1' represents hydrogen, halogen, trifluoromethyl, a 1–3C-alkyl radical, or a 1–3C-alkoxy radical which is optionally completely or predominantly substituted by fluorine, R2 represents hydrogen or a 1–3C-alkyl radical, R3 represents hydrogen or a 1–3C-alkyl or 1–3C-alkoxy radical, R4 represents hydrogen or a 1–3C-alkyl radical and n represents the number 0 or 1, and their salts are new compounds with a marked protective effect on the stomach.

29 Claims, No Drawings

FLUOROALKOXY SUBSTITUTED BENZIMIDAZOLES USEFUL AS GASTRIC ACID SECRETION INHIBITORS

FIELD OF THE INVENTION

The invention relates to new fluoroalkoxy compounds, processes for their preparation, their use and medicaments containing them.

The compounds according to the invention are used in the pharmaceutical industry as intermediates and for the preparation of medicaments.

PRIOR ART

The European Patent Application No. 0 005 129 (=U.S. Pat. No. 4,255,531) describes substituted pyridylsulfinylbenzimidazoles which are said to be potent gastric acid secretion inhibitors. In European Patent Application 0 074 341 the use of a group of benzimidazole derivatives for inhibiting gastric acid secretion is described.

It has now been found, surprisingly, that the fluoroalkoxy compounds which are described below in more detail have interesting and unexpected properties which advantageously distinguish them from the known compounds.

DESCRIPTION OF THE INVENTION

The invention relates to new fluoroalkoxy compounds of formula I

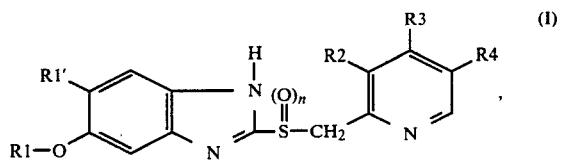

wherein
- $R1$ represents a 1-3C-alkyl radical which is completely or predominantly substituted by fluorine, or a chlorodifluoromethyl radical,
- $R1'$ represents hydrogen, halogen, trifluoromethyl, a 1-3C-alkyl radical or a 1-3C-alkoxy radical which is optionally completely or predominantly substituted by fluorine,
- $R2$ represents hydrogen or a 1-3C-alkyl radical,
- $R3$ represents hydrogen or a 1-3C-alkyl or 1-3C-alkoxy radical,
- $R4$ represents hydrogen or a 1-3C-alkyl radical and
- $n$ represents the number 0 or 1, and the salts of these compounds.

Examples of 1-3C-alkyl radicals which are completely or predominantly substituted by fluorine are the 1,1,2-trifluoroethyl radical, the perfluoropropyl radical, the perfluoroethyl radical and, in particular, the 1,1,2,2-tetrafluoroethyl, the trifluoromethyl, the 2,2,2-trifluoroethyl and the difluoromethyl radical.

Halogen in the context of the present invention is bromine, chlorine and, in particular, fluorine.

1-3C-Alkyl radicals are the propyl, isopropyl, ethyl and, in particular, methyl radical.

Besides the oxygen atom, 1-3C-alkoxy radicals contain the noted 1-3C-alkyl radicals. The methoxy radical is preferred.

Besides the oxygen atom, a 1-3C-alkoxy radical which is completely or predominantly substituted by fluorine contains the previously-mentioned 1-3C-alkyl radicals which are completely or predominantly substituted by fluorine. The 1,1,2,2-tetrafluoroethoxy radical, the trifluoromethoxy radical, the 2,2,2-trifluoroethoxy radical and, in particular, the difluoromethoxy radical may be mentioned.

Illustrative salts of compounds of formula I in which n denotes the number 0 (sulfides) are, above all, the acid-addition salts. The pharmacologically-acceptable salts of the inorganic and organic acids customarily used in galenics are particularly noteworthy. Pharmacologically-unacceptable salts, which may initially be obtained, for example, as process products in the preparation of compounds according to the invention on an industrial scale, are converted into pharmacologically-acceptable salts by processes which are known to the expert. Examples of suitable salts are water-soluble and water-insoluble acid-addition salts, such as the hydrochloride, hydrobromide, hydroiodide, phosphate, nitrate, sulfate, acetate, citrate, gluconate, benzoate, hibenzate, fendizoate, butyrate, sulfosalicylate, maleate, laurate, malate, fumarate, succinate, oxalate, tartrate, amsonate, embonate, metembonate, stearate, tosilate, 2-hydroxy-3-naphthoate, 3-hydroxy-2-naphthoate and mesilate.

Illustrative salts of compounds of formula I in which n denotes the number 1 (sulfoxides) are above all the basic salts, in particular pharmacologically-acceptable salts with inorganic and organic bases customarily used in galenics. Examples of basic salts are the sodium, potassium, calcium or aluminum salts.

Compounds of formula I, wherein $R1$ represents a 1-3C-alkyl radical which is completely or predominantly substituted by fluorine, $R1'$ represents hydrogen, halogen, trifluoromethyl or a 1-3C-alkoxy radical which is completely or predominantly substituted by fluorine, $R2$, $R3$, $R4$ and $n$ have the meaning given above, and their salts, form an embodiment (embodiment a) of the invention.

Compounds of formula I, wherein $R1$ represents a 1-3C-alkyl radical which is completely or predominantly substituted by fluorine, and $R1'$, $R2$, $R3$, $R4$ and $n$ have the meaning given above, and their salts, form another embodiment (embodiment b) of the invention.

Compounds of formula I, wherein $R1'$ represents hydrogen, halogen, trifluoromethyl, or a 1-3C-alkoxy radial which is completely or predominantly substituted by fluorine, and $R1$, $R2$, $R3$, $R4$ and $n$ have the meaning given above, and their salts, form another embodiment (embodiment c) of the invention.

Compounds according to the invention which are noteworthy are those of formula I, wherein $R1$ represents a trifluoromethyl, 1,1,2,2-tetrafluoroethyl, 2,2,2-trifluoroethyl, difluoro methyl or chlorodifluoromethyl radical, $R1'$ represents hydrogen, fluorine, methoxy or difluoromethoxy, $R2$ represents hydrogen or methyl, $R3$ represents hydrogen or methoxy, $R4$ represents hydrogen or methyl and n represents the number 0 or 1, and wherein $R2$, $R3$ and $R4$ are not simultaneously hydrogen atoms, and the salts of these compounds.

Compounds of embodiment a which are noteworthy are those of formula I, wherein $R1$ represents a trifluoromethyl, 1,1,2,2-tetrafluoroethyl, 2,2,2-trifluoroethyl, or difluoromethyl radical, $R1'$ represents hydrogen, fluorine, or difluoromethoxy, $R2$ represents hydrogen or methyl, $R3$ represents hydrogen or methoxy, $R4$ represents hydrogen or methyl and n represents the number 0 or 1, and wherein $R2$, $R3$ and $R4$ are not simultaneously hydrogen atoms, and the salts of these compounds.

Compounds of embodiment b which are noteworthy are those of formula I, wherein R1 represents a trifluoromethyl, 1,1,2,2-tetrafluoroethyl, 2,2,2-trifluoroethyl, or difluoromethyl radical, R1' represents hydrogen, fluorine, methoxy or difluoromethoxy, R2 represents hydrogen or methyl, R3 represents hydrogen or methoxy, R4 represents hydrogen or methyl and n represents the number 0 or 1, and wherein R2, R3 and R4 are not simultaneously hydrogen atoms, and the salts of these compounds.

Compounds of embodiment c which are noteworthy are those of formula I, wherein R1 represents a trifluoromethyl, 1,1,2,2-tetrafluoroethyl, 2,2,2-trifluoroethyl, difluoromethyl, or chlorodifluoromethyl radical, R1' represents hydrogen, fluorine, or difluoromethoxy, R2 represents hydrogen or methyl, R3 represents hydrogen or methoxy, R4 represents hydrogen or methyl and n represents the number 0 or 1, and wherein R2, R3 and R4 are not simultaneously hydrogen atoms, and the salts of these compounds.

Preferred compounds according to the invention are those of formula I, wherein R1 represents a trifluoromethyl, 1,1,2,2-tetrafluoroethyl, 2,2,2-trifluoroethyl, difluoromethyl or chlorodifluoromethyl radical, R1' represents hydrogen, R2 represents hydrogen or methyl, R3 represents methoxy, R4 represents hydrogen or methyl and n represents the number 0 or 1, and the pharmacologically acceptable salts of these compounds.

Preferred compounds according to the invention are furthermore those of formula I, wherein R1 represents a difluoromethyl radical, R1' represents fluorine, methoxy or difluoromethoxy, R2 represents hydrogen or methyl, R3 represents methoxy, R4 represents hydrogen or methyl and n represents the number 0 or 1, and the pharmacologically acceptable salts of these compounds.

Preferred compounds of embodiment a are those of formula I, wherein R1 represents a trifluoromethyl, 1,1,2,2-tetrafluoroethyl, 2,2,2-trifluoroethyl or difluoromethyl radical, R2 represents hydrogen or methyl, R3 represents methoxy, R4 represents hydrogen or methyl and n represents the number 0 or 1, and the pharmacologically acceptable salts of these compounds.

Preferred compounds of embodiment b are those of formula I, wherein R1 represents a trifluoromethyl, 1,1,2,2-tetrafluoroethyl, 2,2,2-trifluoroethyl or difluoromethyl radical, R1' represents fluorine, methoxy or difluoromethoxy, R2 represents hydrogen or methyl, R3 represents methoxy, R4 represents hydrogen or methyl and n represents the number 0 or 1, and the pharmacologically acceptable salts of these compounds.

Preferred compounds of embodiment c are those of formula I, wherein R1 represents a trifluoromethyl, 1,1,2,2-tetrafluoroethyl, 2,2,2-trifluoroethyl, difluoromethyl or chlorodifluoromethyl radical, R1' represents hydrogen, R2 represents hydrogen or methyl, R3 represents methoxy, R4 represents hydrogen or methyl and n represents the number 0 or 1, and the pharmacologically acceptable salts of these compounds.

Examples of compounds according to the invention are:
2-[(4-ethoxy-3-methyl-2-pyridyl)methylthio]-5-trifluoromethoxy-1H-benzimidazole,
2-[(4-ethoxy-3-methyl-2-pyridyl)methylsulfinyl)-5-trifluoromethoxy-1H-benzimidazole,
2-[(3-methyl-2-pyridyl)methylthio]-5-trifluoromethoxy-1H-benzimidazole,
2-[(3-methyl-2-pyridyl)methylsulfinyl]-5-trifluoromethoxy-1H-benzimidazole,
2-[(5-methyl-2-pyridyl)methylthio]-5-trifluoromethoxy-1H-benzimidazole,
2-[(5-methyl-2-pyridyl)methylsulfinyl)-5-trifluoromethoxy-1H-benzidazol,
2-[(3,5-dimethyl-2-pyridyl)methylthio]-5-trifluoromethoxy-1H-benzimidazole,
2-[(3,5-dimethyl-2-pyridyl)methylsulfinyl]-5-trifluoromethoxy-1H-benzimidazole,
2-[(4-ethoxy-3-methyl-2-pyridyl)methylthio]-5-(1,1,2,2-tetrafluoroethoxy)-1H-benzimidazole,
2-[(4-ethoxy-3-methyl-2-pyridyl)methylsulfinyl]-5-(1,1,2,2-tetrafluoroethoxy)-1H-benzimidazole,
2-[(4-methoxy-3-methyl-2-pyridyl)methylthio]-5-pentafluoroethoxy-1H-benzimidazole,
2-[(4-methoxy-3-methyl-2-pyridyl)methylsulfinyl]-5-pentafluoroethoxy-1H-benzimidazole,
2-[(4-methoxy-5-methyl-2-pyridyl)methylthio]-5-pentafluoroethoxy-1H-benzimidazole,
2-[(4-methoxy-5-methyl-2-pyridyl)methylsulfinyl]-5-pentafluoroethoxy-1H-benzimidazole,
5-heptafluoropropoxy-2-[(4-methoxy-3-methyl-2-pyridyl)methylthio]-1H-benzimidazole,
5-heptafluoropropoxy-2-[(4-methoxy-3-methyl-2-pyridyl)methylsulfinyl]-1H-benzimidazole,
5-heptafluoropropoxy-2-[(4-methoxy-5-methyl-2-pyridyl)methylthio]-1H-benzimidazole,
5-heptafluoropropoxy-2-[(4-methoxy-5-methyl-2-pyridyl)methylsulfinyl]-1H-benzimidazole,
2-[(4-methoxy-5-methyl-2-pyridyl)methylthio]-5-(2,2,2-trifluoroethoxy)-1H-benzimidazole,
2-[(4-methoxy-5-methyl-2-pyridyl)methylsulfinyl]-5-(2,2,2-trifluoroethoxy)-1H-benzimidazole,
2-[(4-methoxy-3,5-dimethyl-2-pyridyl)methylthio]-5-(2,2,2-trifluoroethoxy)-1H-benzimidazole,
2-[(4-methoxy-3,5-dimethyl-2-pyridyl)methylsulfinyl]-5-(2,2,2-trifluoro-ethoxy)-1H-benzimidazole,
2-[(4-ethoxy-3-methyl-2-pyridyl)methylthio]-5-(2,2,2-trifluoroethoxy)-1H-benzimidazole,
2-[(4-ethoxy-3-methyl-2-pyridyl)methylsulfinyl]-5-(2,2,2-trifluoroethoxy)-1H-benzimidazole,
2-[(3-methyl-2-pyridyl)methylthio]-5-(2,2,2-trifluoroethoxy)-1H-benzimidazole,
2-[(3-methyl-2-pyridyl)methylsulfinyl]-5-(2,2,2-trifluoroethoxy)-1H-benzimidazole,
2-[(4-methoxy-2-pyridyl)methylthio]-5-(1,1,2-trifluoroethoxy)-1H-benzimidazole,
2-[(4-methoxy-2-pyridyl)methylsulfinyl)-5-(1,1,2-trifluoroethoxy)-1H-benzimidazole,
2-[(4-methoxy-3-methyl-2-pyridyl)methylthio]-5-(1,1,2-trifluoroethoxy)-1H-benzimidazole,
2-[(4-methoxy-3-methyl-2-pyridyl)methylsulfinyl]-5-(1,1,2-trifluoroethoxy)-1H-benzimidazole,
2-[(4-methoxy-5-methyl-2-pyridyl)methylthio]-5-(1,1,2-trifluoroethoxy)-1H-benzimidazole,
2-[(4-methoxy-5-methyl-2-pyridyl)methylsulfinyl]-5-(1,1,2-trifluoroethoxy)-1H-benzimidazole,
2-[(4-methoxy-3,5-methyl-2-pyridyl)methylthio]-5-(1,1,2-trifluoroethoxy)-1H-benzimidazole,
2-[(4-methoxy-3,5-methyl-2-pyridyl)methylsulfinyl]-5-(1,1,2-trifluoroethoxy)-1H-benzimidazole,
2-[(4-ethoxy-3-methyl-2-pyridyl)methylthio]-5-(1,1,2-trifluoroethoxy)-1H-benzimidazole, 2-[(4-ethoxy-3-methyl-2-pyridyl)methylsulfinyl]-5-(1,1,2-trifluoroethoxy)-1H-benzimidazole,
2-[(3-methyl-2-pyridyl)methylthio]-5-(1,1,2-trifluoroethoxy)-1H-benzimidazole,
2-[(3-methyl-2-pyridyl)methylsulfinyl]-5-(1,1,2-trifluoroethoxy)-1H-benzimidazole,
6-fluoro-2-[(4-methoxy-3-methyl-2-pyridyl)methylthio]-5-trifluoromethoxy-1H-benzimidazole,
6-fluoro-2-[(4-methoxy-3-methyl-2-pyridyl)methylsulfinyl]-5-trifluoromethoxy-1H-benzimidazole,
2-[(4-methoxy-3-methyl-2-pyridyl)methylthio]-5-trifluoromethoxy-6-trifluoromethyl-1H-benzimidazole,
2-[(4-methoxy-3-methyl-2-pyridyl)methylsulfinyl]-5-trifluoromethoxy-6-trifluoromethyl-1H-benzimidazole,
5,6-bis(trifluoromethoxy)-2-[(4-methoxy-5-methyl-2-pyridyl)methylthio]-1H-benzimidazole,
5,6-bis(trifluoromethoxy)-2-[(4-methoxy-5-methyl-2-pyridyl)methylsulfinyl]-1H-benzimidazole,
2-[(3-methyl-2-pyridyl)methylthio-5-trifluoromethoxy-6-trifluoromethyl-1H-benzimidazole,
2-[(3-methyl-2-pyridyl)methylsulfinyl]-5-trifluoromethoxy-6-trifluoromethyl-1H-benzimidazole,
6-fluoro-2-[(4-methoxy-3-methyl-2-pyridyl)methylthio]-5-(1,1,2,2-tetrafluoroethoxy)-1H-benzimidazole,
6-fluoro-2-[(4-methoxy-3-methyl-2-pyridyl)methylsulfinyl]-5-(1,1,2,2-tetrafluoroethoxy)-1H-benzimidazole,
2-[(4-methoxy-5-methyl-2-pyridyl)methylthio]-5-(1,1,2,2-tetrafluoroethoxy)-6-trifluoromethyl-1H-benzimidazole,
2-[(4-methoxy-5-methyl-2-pyridyl)methylsulfinyl]-5-(1,1,2,2-tetrafluoroethoxy)-6-trifluoromethyl-1H-benzimidazole,
5,6-bis(1,1,2,2-tetrafluoroethoxy)-2-[(4-methoxy-3,5-dimethyl-2-pyridyl)methylthio]-1H-benzimidazole,
5,6-bis(1,1,2,2-tetrafluoroethoxy)-2-[(4-methoxy-3,5-dimethyl-2-pyridyl)methylsulfinyl]-1H-benzimidazole,
2-[(3-methyl-2-pyridyl)methylthio]-5-(1,1,2,2-tetrafluoroethoxy)-6-trifluoromethoxy-1H-benzimidazole,
2-[(3-methyl-2-pyridyl)methylsulfinyl]-5-(1,1,2,2-tetrafluoroethoxy)-6-trifluoromethoxy-1H-benzimidazole,
2-[(4-methoxy-2-pyridyl)methylthio]-5-pentafluoroethoxy-1H-benzimidazole,
2-[(4-methoxy-2-pyridyl)methylsulfinyl]-5-pentafluoroethoxy-1H-benzimidazole,
2-[(5-methyl-2-pyridyl)methylthio]-5-(1,1,2,2-tetrafluoroethoxy)-1H-benzimidazole,
2-[(5-methyl-2-pyridyl)methylsulfinyl]-5-(1,1,2,2-tetrafluoroethoxy)-1H-benzimidazole,
2-[(3,5-dimethyl-2-pyridyl)methylthio]-5-(1,1,2,2-tetrafluoroethoxy)-1H-benzimidazole,
2-[(3,5-dimethyl-2-pyridyl)methylsulfinyl]-5-(1,1,2,2-tetrafluoroethoxy)-1H-benzimidazole,
2-[(4-methoxy-2-pyridyl)methylthio]-5,6-bis(trifluoromethoxy)-1H-benzimidazole,
2-[(4-methoxy-2-pyridyl)methylsulfinyl]-5,6bis(trifluoromethoxy)-1H-benzimidazole,
2-[(4-methoxy-3-methyl-2-pyridyl)methylthio]-5,6-bis(trifluoromethoxy)-1H-benzimidazole,
2-[(4-methoxy-3-methyl-2-pyridyl)methylsulfinyl]-5,6-bis(trifluoromethoxy)-1H-benzimidazole,
2-[(4-methoxy-2-pyridyl)methylthio]-5,6-bis(1,1,2,2-tetrafluoroethoxy)-1H-benzimidazole,
2-[(4-methoxy-2-pyridyl)methylsulfinyl]-5,6-bis(1,1,2,2-tetrafluoroethoxy)-1H-benzimidazole,
2-[(4-methoxy-3-methyl-2-pyridyl)methylthio]-5,6-bis(1,1,2,2-tetrafluoroethoxy)-1H-benzimidazole,
2-[(4-methoxy-3-methyl-2-pyridyl)methylsulfinyl]-5,6-bis(1,1,2,2-tetrafluoroethoxy)-1H-benzimidazole,
5-difluoromethoxy-2-[(4-methoxy-5-methyl-2-pyridyl)methylthio]-1H-benzimidazole,
5-difluoromethoxy-2-[(4-methoxy-5-methyl-2-pyridyl)methylsulfinyl]-1H-benzimidazole,
5-difluoromethoxy-2-[(4-methoxy-3,5-dimethyl-2-pyridyl)methylthio]-1H-benzimidazole,
5-difluoromethoxy-2-[(4-methoxy-3,5-dimethyl-2-pyridyl)methylsulfinyl]-1H-benzimidazole,
5-difluoromethoxy-2-[(3-methyl-2-pyridyl)methylthio]-1H-benzimidazole,
5-difluoromethoxy-2-[(3-methyl-2-pyridyl)methylsulfinyl]-1H-benzimidazole,
5-difluoromethoxy-2-[(5-methyl-2-pyridyl)methylthio]-1H-benzimidazole,
5-difluoromethoxy-2-[(5-methyl-2-pyridyl)methylsulfinyl]-1H-benzimidazol,
5-difluoromethoxy-2-[(3,5-dimethyl-2-pyridyl)methylthio]-1H-benzimidazole,
5-difluoromethoxy-2-[(3,5-dimethyl-2-pyridyl)methylsulfinyl]-1H-benzimidazole,
5-chlorodifluoromethoxy-2-[(4-methoxy-3-methyl-2-pyridyl)methylthio]-1H-benzimidazole,
5-chlorodifluoromethoxy-2-[(4-methoxy-3-methyl-2-pyridyl)methylsulfinyl]-1H-benzimidazole,
5-chlorodifluoromethoxy-2-[(3-methyl-2-pyridyl)methylthio]-1H-benzimidazole,
5-chlorodifluoromethoxy-2-[(3-methyl-2-pyridyl)methylsulfinyl]-1H-benzimidazole,
5,6-bis(difluoromethoxy)-2-[(4-methoxy-5-methyl-2-pyridyl)methylthio]-1H-benzimidazole,
5,6-bis(difluoromethoxy)-2-[(4-methoxy-5-methyl-2-pyridyl)methylsulfinyl]-1H-benzimidazole,
5,6-bis(difluoromethoxy)-2-[(4-methoxy-3,5-dimethyl-2-pyridyl)methylthio]-1H-benzimidazole,
5,6-bis(difluoromethoxy)-2-[(4-methoxy-3,5-dimethyl-2-pyridyl)methylsulfinyl]-1H-benzimidazole,
5,6-bis(difluoromethoxy)-2-[(3-methyl-2-pyridyl)methylthio]-1H-benzimidazole,
5,6-bis(difluoromethoxy)-2-[(3-methyl-2-pyridyl)methylsulfinyl]-1H-benzimidazole,
5-difluoromethoxy-6-fluoro-2-[(4-methoxy-3-methyl-2-pyridyl)methylthio]-1H-benzimidazole,
5-difluoromethoxy-6-fluoro-2-[(4-methoxy-3-methyl-2-pyridyl)methylsulsfinyl)-1H-benzimidazole,
5-difluoromethoxy-6-methoxy-2-[(4-methoxy-5-methyl-2-pyridyl)methylthio]-1H-benzimidazole,
5-difluoromethoxy-6-methoxy-2-[(4-methoxy-5-methyl-2-pyridyl)methylsulfinyl]-1H-benzimidazole,
5-difluoromethoxy-6-methoxy-2-[(4-methoxy-3,5-dimethyl-2-pyridyl)methylthio]-1H-benzimidazole,
5-difluoromethoxy-6-methoxy-2-[(4-methoxy-3,5-dimethyl-2-pyridyl)methylsulfinyl]-1H-benzimidazole,
5-difluoromethoxy-6-methoxy-2-[(3-methyl-2-pyridyl)methylthio]-1H-benzimidazole,
5-difluoromethoxy-6-methoxy-2-[(3-methyl-2-pyridyl)methylsulfinyl]-1H-benzimidazole,
5-difluoromethoxy-6-methoxy-2-[(5-methyl-2-pyridyl)methylthio]-1H-benzimidazole,
5-difluoromethoxy-6-methoxy-2-[(5-methyl-2-pyridyl)methylsulfinyl]-1H-benzimidazole,
5-difluoromethoxy-6-methoxy-2-[(3,5-dimethyl-2-pyridyl)methylthio]-1H-benzimidazole,
5-difluoromethoxy-6-methoxy-2-[(3,5-dimethyl-2-pyridyl)methylsulfinyl]-1H-benzimidazole, 5-methoxy-2-[(4-methoxy-2-pyridyl)methylthio]-6-trifluoromethoxy-1H-benzimidazole,
5-methoxy-2-[(4-methoxy-2-pyridyl)methylsulfinyl]-6-trifluoromethoxy-1H-benzimidazole,
5-methoxy-2-[(4-methoxy-3-methyl-2-pyridyl)methylthio]-6-trifluoromethoxy-1H-benzimidazole,
5-methoxy-2-[(4-methoxy-3-methyl-2-pyridyl)methylsulfinyl]-6-trifluoromethoxy-1H-benzimidazole,
5-methoxy-2-[(4-methoxy-5-methyl-2-pyridyl)methylthio]-6-trifluoromethoxy-1H-benzimidazole,
5-methoxy-2-[(4-methoxy-5-methyl-2-pyridyl)methylsulfinyl]-6-trifluoromethoxy-1H-benzimidazole,
5-methoxy-2-[(4-methoxy-3,5-dimethyl-2-pyridyl)methylthio]-6-trifluoromethoxy-1H-benzimidazole,
5-methoxy-2-[(4-methoxy-3,5-dimethyl-2-pyridyl)methylsulfinyl]-6-trifluoromethoxy-1H-benzimidazole,
5-methoxy-2-[(3-methyl-2-pyridyl)methylthio]-6-trifluoromethoxy-1H-benzimidazole,
5-methoxy-2-[(3-methyl-2-pyridyl)methylsulfinyl]-6-trifluoromethoxy-1H-benzimidazole,
b 5-methoxy-2-[(5-methyl-2-pyridyl)methylthio]-6-trifluoromethoxy-1H-benzimidazole,
5-methoxy-2-[(5-methyl-2-pyridyl)methylsulfinyl]-6-trifluoromethoxy-1H-benzimidazole, 5-methoxy-2-[(4-methoxy-2-pyridyl)methylthio]-6-(1,1,2,2-tetrafluoroethoxy)-1H-bnzimidazole,
5-methoxy-2-[(4-methoxy-2-pyridyl)methylsulfinyl]-6-(1,1,2,2-tetrafluoroethoxy)-1H-benzimidazole,
5-methoxy-2-[(4-methoxy-3-methyl-2-pyridyl)methylthio]-6-(1,1,2,2-tetrafluoroethoxy)-1H-benzimidazole,
5-methoxy-2-[(4-methoxy-3-methyl-2-pyridyl)methylsulfinyl]-6-(1,1,2,2-tetrafluoroethoxy)-1H-benzimidazole,
5-methoxy-2-[(4-methoxy-5-methyl-2-pyridyl)methylthio]-6-(1,1,2,2-tetrafluoroethoxy)-1H-benzimidazole,
5-methoxy-2-[(4-methoxy-5-methyl-2-pyridyl)methylsulfinyl]-6-(1,1,2,2-tetrafluoroethoxy)-1H-benzimidazole,
5-methoxy-2-[(4-methoxy-3,5-dimethyl-2-pyridyl)methylthio]-6-(1,1,2,2-tetrafluoroethoxy)-1H-benzimidazole,
5-methoxy-2-[(4-methoxy-3,5-dimethyl-2-pyridyl)methylsulfinyl]-6-(1,1,2,2-tetrafluoroethoxy)-1H-benzimidazole,
5-difluoromethoxy-2-[(4-methoxy-2-pyridyl)methylthio]-6-methyl-1H-benzimidazol,
5-difluoromethoxy-2-[(4-methoxy-2-pyridyl)methylsulfinyl]-6-methyl-1H-benzimidazole,
5-difluoromethoxy-2-[(4-methoxy-3-methyl-2-pyridyl)methylthio]-6-methyl-1H-benzimidazole,
5-difluoromethoxy-2-[(4-methoxy-3-methyl-2-pyridyl)methylsulfinyl]-6-methyl-1H-benzimidazole,
5-difluoromethoxy-1-[(4-methoxy-2-pyridyl)methylthio]-6-(1,1,2,2-tetrafluoroethoxy)-1H-benzimidazole,
5-difluoromethoxy-1-[(4-methoxy-2-pyridyl)methylsulfinyl]-6-(1,1,2,2-tetrafluoroethoxy)-1H-benzimidazole,
5-difluoromethoxy-1-[(4-methoxy-3-methyl-2-pyridyl)methylthio]-6-(1,1,2,2-tetrafluoroethoxy)-1H-benzimidazole,
5-difluoromethoxy-1-[(4-methoxy-3-methyl-2-pyridyl)methylsulfinyl]-6-(1,1,2,2-tetrafluoroethoxy)-1H-benzimidazole
and their salts.

Because of tautomerism in the imidazole ring, 5-substitution in the benzimidazole is identical to 6-substitution.

The invention furthermore relates to a process for the preparation of the fluoroalkoxy compounds of formula I, wherein R1, R1', R2, R3, R4 and n have the previously-ascribed meanings, and their salts.

The process is characterized in that
(a) mercaptobenzimidazoles of formula II are reacted with picoline derivatives III

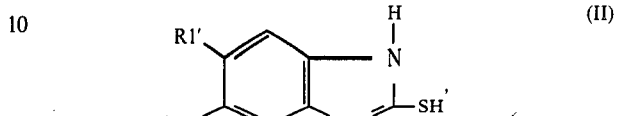

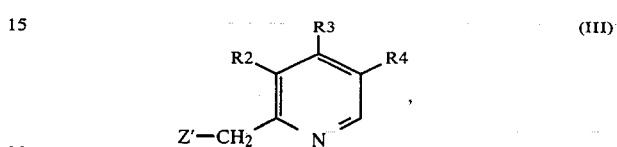

or (b) benzimidazoles of formula IV are reacted with mercaptopicolines V

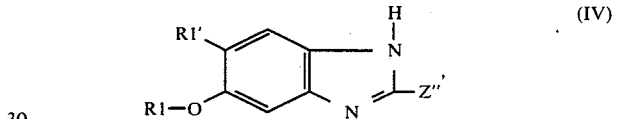

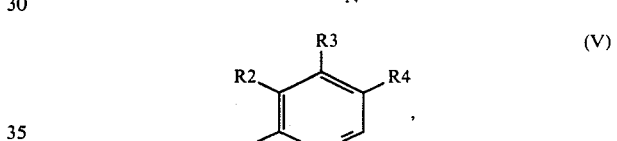

or (c) o-phenylenediamines of formula VI are reacted with formic acid derivatives VII

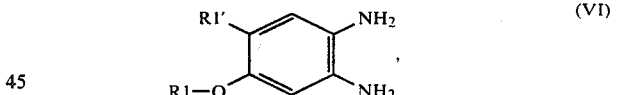

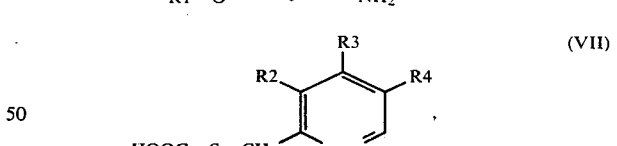

and, when appropriate, the 2-benzimidazolyl 2-pyridyl sulfides obtained according to (a), (b) or (c), of formula VIII

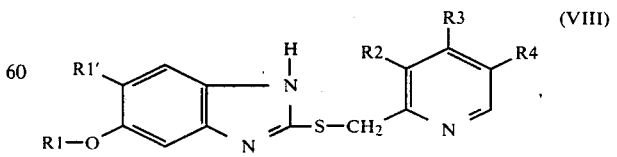

are then oxidized and/or converted into the salts, or in that
(d) benzimidazoles of formula IX are reacted with pyridine derivatives X

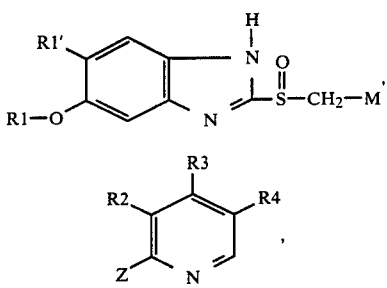

(IX)

(X)

or (e) sulfinyl derivatives of formula XI are reacted with 2-picoline derivatives XII

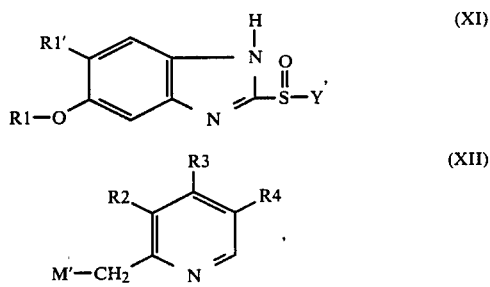

(XI)

(XII)

and, when appropriate, the products are then converted into salts, Y, Z, Z' and Z" representing suitable leaving groups, H representing an alkali metal atom (Li, Na or K). M' representing the equivalent of a metal atom and R1, R1', R2, R3, R4 and n having the afore-mentioned meanings.

In the described reactions, compounds II–XII are used as such or, when appropriate, in the form of their salts.

Preparation processes (a), (b) and (c) lead to sulfides according to the invention, and the oxidation of compounds VIII and processes (d) and (e) yield sulfoxides according to the invention.

The expert is familiar with which leaving groups Y, Z, Z' and Z" are suitable, on the basis of his expert knowledge. A suitable leaving group Y is, for example, a group which forms a reactive sulfinic acid derivative together with the sulfinyl group to which it is bonded. Examples of suitable leaving groups Y are alkoxy, dialkylamino and alkylmercapto groups. Examples of suitable leaving groups Z, Z' and Z" are halogen atoms, in particular chlorine atoms, or hydroxyl groups activated by esterification (for example with p-toluenesulfonic acid). The equivalent of a metal atom M' is, for example, an alkali metal atom (Li, Na or K) or an alkaline earth metal atom (for example Mg), which is substituted by a halogen atom (for example Br, Grignard reagent), or any other optionally substituted metal atom which is known to react like the mentioned metals in substitution reactions of organometallic compounds.

The reaction of II with III is carried out in a manner which is known per se in suitable solvents, preferably polar protic or aprotic solvents (such as methanol, isopropanol, dimethylsulfoxide, acetone, dimethylformamide or acetonitrile), with addition or in the absence of water. It is carried out, for example, in the presence of a proton acceptor. Suitable proton acceptors are alkalimetal hydroxides, such as sodium hydroxide; alkali metal carbonates, such as potassium carbonate; or tertiary amines, such as pyridine, triethylamine or ethyldiisopropylamine. Alternatively, the reaction is carried out without proton acceptors, in which case—depending on the nature of the starting compounds—the acid-addition salts are initially optionally separated off in a particularly pure form. The reaction temperature is ordinarily between 0° and 150° C., preferred temperatures being between 20° C. and 80° C. in the presence of proton acceptors, between 60° and 120° C. without proton acceptors—and, in particular, at the boiling point of the solvents used. The reaction times are between 0.5 and 12 hours.

Similar reaction conditions to those for the reaction of II with III are used in the reaction of IV with V, which is carried out in a manner which is known per se.

The reaction of VI with VII is preferably carried out in polar (optionally water-containing) solvents in the presence of a strong acid, for example hydrochloric acid, in particular at the boiling point of the solvent used.

The sulfides VIII are oxidized in a manner which is known per se under conditions with which the expert is familiar for the oxidation of sulfides to sulfoxides [in this context, see, for example, J. Drabowicz and M. Mikolajczyk, Organic preparations and procedures int. 14(1-2), 45–89 (1982) or E. Block in S.Patai, The Chemistry of Functional Groups, Supplement E, Part 1, pages 539 to 608, John Wiley and Sons (Interscience Publication), 1980]. Possible oxidizing agents are all the reagents usually employed for the oxidation of sulfides, in particular peroxyacids, such as peroxyacetic acid, trifluoroperoxyacetic acid, 3,5-dinitroperoxybenzoic acid, peroxymaleic acid or, preferably, m-chloroperoxybenzoic acid.

The reaction temperature is between −70° C. and the boiling point of the solvent used (depending on the reactivity of the oxidizing agent and the degree of dilution), but is preferably between −30° C. and +20° C. Oxidation with halogens or with hypohalites (for example with aqueous sodium hypochlorite solution) has also proved advantageous, and is appropriately carried out at temperatures between 0° C. and 30° C. The reaction is advantageously carried out in inert solvent, for example aromatic or chlorinated hydrocarbons, such as benzene, toluene, methylene chlorid or chloroform, preferably in esters, such as ethyl acetate or isopropyl acetate, or ethers, such as dioxane.

The reaction of IX with X is preferably carried out in inert solvent, such as those which are also usually employed for the reaction of enolate ions with alkylating agents. Examples which may be mentioned are aromatic solvents, such as benzene or toluene. The reaction temperature is, as a rule, between 0° and 120° C. (depending on the nature of the alkali metal atom M and the leaving group Z), the boiling point of the solvent used being preferred. For example [when M represents Li (lithium) and Z represents Cl (chlorine) and the reaction is carried out in benzene] the boiling point of benzene (80° C.) is preferred.

Compounds XI are reacted with compounds XII in a manner which is known per se, such as that with which the expert is familiar for the reaction of organometallic compounds.

The compounds according to the invention are first obtained either as such or in the form of their salts, depending on the nature of the starting compounds, which are optionally employed, when appropriate, in the form of their salts, and depending on the reaction conditions.

The salts are otherwise obtained by dissolving the free compounds in a suitable solvent, for example in a chlorinated hydrocarbon, such as methylene chloride or chloroform, a low-molecular aliphatic alcohol (ethanol or isopropanol), an ether (diisopropyl ether), a ketone (acetone), or water, which contains the desired acid or base or to which the desired acid or base—when appropriate in the exactly calculated stoichiometric amount—is then added.

The salts are isolated by filtration, reprecipitation or precipitation or by evaporation of solvent.

Salts obtained are converted into the corresponding free compounds by alkalization or acidification, for example with aqueous sodium bicarbonate or with dilute hydrochloric acid, and the free compounds are in turn converted into the salts. In this manner, the compounds are purified or pharmacologically-unacceptable salts are converted into pharmacologically-acceptable salts.

The sulfoxides according to the invention are optically-active compounds. The invention thus relates both to the enantiomers and to their mixtures and racemates. The enantiomers are separated in a manner which is known per se (for example by preparation and separation of corresponding diastereomeric compounds). However, the enantiomers are alternatively prepared by asymmetric synthesis, for example by reacting optically-active pure compounds XI or diastereomeric pure compounds XI with compounds XII [in this context, see K. K. Andersen, Tetrahedron Lett., 93 (1962)].

The compounds according to the invention are preferably synthesized by reaction of II with III and, when appropriate, subsequent oxidation of the sulfide VIII formed.

Compounds of formula II are new and are likewise the subject of the invention. Compounds III–VII and IX–XII are either known or they are readily prepared analogously to known compounds from available starting materials. Compounds II are obtained, for example, by reacting compounds VI with carbon disulfides in a reaction mixture containing alkali-metal hydroxide or alkali-metal O-ethyldithiocarbonate. Compounds III are prepared in accordance with the method of O. E. Schulz and S. Fedders, Arc. Pharm. (Weinheim) 310, 128–136 (1977).

Compounds VI are synthesized by preparation method shown in the following equation A:

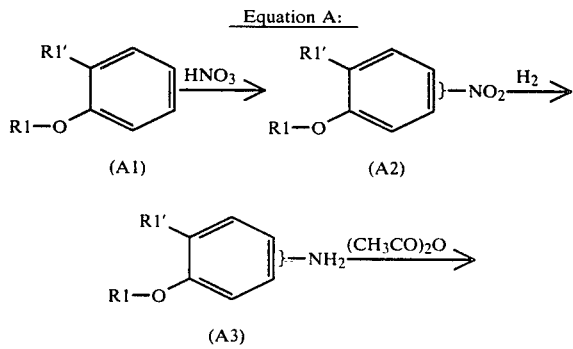

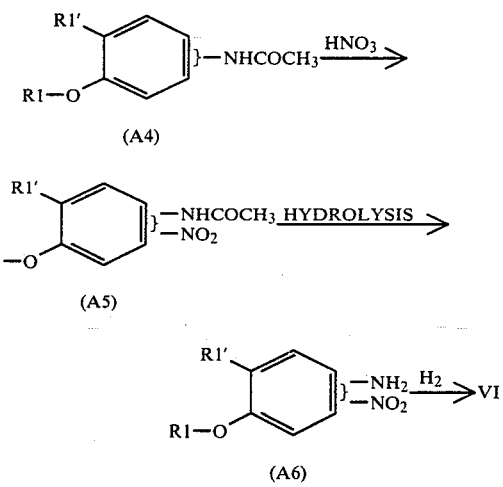

The starting compounds A1–A3 are prepared by known or analogous methods [for example J.Org.Chem. 44, 2907–2910 (1979); J.Org.Chem. 29, 1–11 (1964); German Offenlegungsschrift 2,029,556; J. Fluorine Chem. 18, 281–91 (1981); and Synthesis 1980, 727–8], it also being possible for isomer mixtures to be formed when substituents R1' and R1-O are not identical.

Compounds IX are obtained, for example, from compounds II by methylation, oxidation and subsequent deprotonation—for example with alkali metal hydrides or alcoholates or customary organometallic compounds. Compounds X are prepared in accordance with the method of Z. Talik, Roczniki Chem. 35, 475 (1961).

The following examples illustrate the invention in more detail without limiting it. "m.p." denotes melting point; the abbreviation "h" is used for hour(s); the abbreviation "min." is used for minutes. "Ether" is understood as meaning diethyl ether.

EXAMPLES

1.

2-[(4-Methoxy-2-pyridyl)methylsulfinyl]-5-trifluoromethoxy-1H-benzimidazole

A solution of 1.45 g of 85% pure m-chloroperoxybenzoic acid in 20 ml of methylene chloride is added dropwise to a solution of 2.4 g of 2-[4-methoxy-2-pyridyl)-methylthio]-5-trifluoromethoxy-1H-benzimidazole in 30 ml of methylene chloride at −30° C. in the course of 20 min., with thorough stirring. Stirring is continued at −30° C. for a further h, the temperature is allowed to rise gradually to −10° C., 1 ml of triethylamine is added and the solution is washed at 0°–10° C. with 1M potassium bicarbonate solution and then with water and dried with magnesium sulfate. The solvent is distilled off in vacuo at a maximum temperature of 30° C. and the residue is crystallized from ether. 2.2 g (86%) of the title compound are obtained. M.p. 150°–152° C. (decomposition).

The following compounds are obtained analogously:
2-[(4-methoxy-3-methyl-2-pyridyl)methylsulfinyl]-5-trifluoromethoxy-1H-benzimidazole of m.p. 165°–166° C. (decomposition) from methanol, in 65% yield,
2-[(4-methoxy-5-methyl-2-pyridyl)methylsulfinyl]-5-trifluoromethoxy-1H-benzimidazole of m.p. 170°–172° C. (decomposition) from ethyl acetate, in 91% yield, 2-[(4-methoxy-3,5-dimethyl-2-pyridyl)methylsulfinyl]-5-trifluoromethoxy-1H-benzimidazole of m.p. 160°–162° C. (decomposition) from ethyl acetate, in 75% yield, 2-[(4-methoxy-2-pyridyl)methylsulfiny]-5-(1,1,2,2-tetrafluoroethoxy)-1H-benzimidazole of m.p. 131°–132° C. (decomposition) from diisopropyl ether, in 93% yield, 2-[(4-methoxy-3-methyl-2-pyridyl)methylsulfiny]-5-(1,1,2,2-tetrafluoroethoxy)-1H-benzimidazole of m.p. 135°–136° C. (decomposition) from ethyl acetate/petroleum ether (50° C./70° C.), in 77% yield, 2-[(4-methoxy-5-methyl-2-pyridyl)methylsulfiny]-5-(1,1,2,2-tetrafluoroethoxy)-1H-benzimidazole of m.p. 163°–164° C. (decomposition) from diisopropyl ether, in 93% yield, 2-[(3-methyl-2-pyridyl)methylsulfiny]-5-(1,1,2,2-tetrafluoroethoxy)-1H-benzimidazole of m.p. 110°–111° C. (decomposition) from diisopropyl ether, in 61% yield.

2-[(4-methoxy-3,5-dimethyl-2-pyridyl)methylsulfiny]-5-(1,1,2,2-tetrafluoroethoxy)-1H-benzimidazole of m.p. 132°–133° C. (decomposition) from ether, in 59% yield, 2-[(4-methoxy-2-pyridyl)methylsulfinyl]-5-(2,2,2-trifluoroethoxy)-1H-benzimidazole of m.p. 95°–97° C. from ether, in 69% yield, 2-[(4-methoxy-3-methyl-2-pyridyl)methylsulfinyl]-5-(2,2,2-trifluoroethoxy)-1H-benzimidazole of m.p. 172°–173° C. (decomposition) from acetonitrile, in 81% yield, 5-chlorodifluoromethoxy-2-[(4-methoxy-2-pyridyl)methylsulfinyl]-1H-benzimidazole of m.p. 154°–156° C. (decomposition) from ethyl acetate in 65% yield.

5-difluoromethoxy-2-[(4-methoxy-2-pyridyl)methylsulfinyl]-1H-benzimidazole of m.p. 159°–161° C. (decomposition) from ethyl acetate in 74% yield, 5-difluoromethoxy-2-[(4-methoxy-3-methyl-2-pyridyl)methylsulfinyl]-1H-benzimidazole of m.p. 166°–168° C. (decomposition) from ethyl acetate in 77% yield, 5,6-bis(difluoromethoxy)-2-[(4-methoxy-2-pyridyl)methylsulfinyl]-1H-benzimidazole of m.p. 173°–175° C. (decomposition) from ethyl acetate in 60% yield, 5,6-bis(difluoromethoxy)-2-[(4-methoxy-3-methyl-2-pyridyl)methylsulfinyl]-1H-benzimidazole of m.p. 184°–185° C. (decomposition) from ethyl acetate in 50% yield, 5-difluoromethoxy-6-fluoro-2-[(4-methoxy-2-pyridyl)methylsulfinyl]-1H-benzimidazole of m.p. 160°–162° C. (decomposition) from ethyl acetate in 54% yield, 5-difluoromethoxy-6-methoxy-2-[(4-methoxy-2-pyridyl)methylsulfinyl]-1H-benzimidazole of m.p. 180°–181° C. (decomposition) from ethyl acetate in 88% yield, 5-difluoromethoxy-6-methoxy-2-[(4-methoxy-3-methyl-2-pyridyl)methylsulfinyl]-1H-benzimidazole of m.p. 94°–96° C. (decomposition) from ethyl acetate in 89% yield, by reacting 2-[(4-methoxy-3-methyl-2-pyridyl)methylthio]-5-trifluoromethoxy-1H-benzimidazole, 2-[(4-methoxy-5-methyl-2-pyridyl)methylthio]-5-trifluoromethoxy-1H-benzimidazole, 2-[(4-methoxy-3,5-dimethyl-2-pyridyl)methylthio]-5-trifluoromethoxy-1H-benzimidazole, 2-[(4-methoxy-2-pyridyl)methylthio]-5-(1,1,2,2-tetrafluoroethoxy)-1H-benzimidazole, 2-[(4-methoxy-3-methyl-2-pyridyl)methylthio]-5-(1,1,2,2-tetrafluoroethoxy)-1H-benzimidazole, 2-[(4-methoxy-5-methyl-2-pyridyl)methylthio]-5-(1,1,2,2-tetrafluoroethoxy)-1H-benzimidazole, 2-[(3-methyl-2-pyridyl)methylthio]-5-(1,1,2,2-tetrafluoroethoxy)-1H-benzimidazole, 2-[(4-methoxy-3,5-dimethyl-2-pyridyl)methylthio]-5-(1,1,2,2-tetrafluoroethoxy)-1H-benzimidazole, 2-[(4-methoxy-2-pyridyl)methylthio]-5-(2,2,2-trifluoroethoxy)-1H-benzimidazole, 2-[(4-methoxy-3-methyl-2-pyridyl)methylthio]-5-(2,2,2-trifluoroethoxy)-1H-benzimidazole, 5-chlorodifluoromethoxy-2-[(4-methoxy-2-pyridyl)methylthio]-1H-benzimidazole, 5-difluoromethoxy-2-[(4-methoxy-2-pyridyl)methylthio]-1H-benzimidazole, 5-difluoromethoxy-2-[(4-methoxy-3-methyl-2-pyridyl)methylthio]-1H-benzimidazole, 5,6-bis(difluoromethoxy)-2-[(4-methoxy-2-pyridyl)methylthio]-1H-benzimidazole, 5,6-bis(difluoromethoxy)-2-[(4-methoxy-3-methyl-2-pyridyl)methylthio]-1H-benzimidazole, 5-difluoromethoxy-6-fluoro-2-[(4-methoxy-2-pyridyl)methylthio]-1H-benzimidazole, 5-difluoromethoxy-6-methoxy-2-[(4-methoxy-2-pyridyl)methylthio]-1H-benzimidazole and 5-difluoromethoxy-6-methoxy-2-[(4-methoxy-3-methyl-2-pyridyl)methylthio]-1H-benzimidazole, with m-chloroperoxybenzoic acid.

2.

2-[(4-Methoxy-2-pyridyl)methylsulfinyl]-5-(1,1,2,2-tetrafluoroethoxy)-1H-benzimidazole A mixture of 8.5 ml of commercially available sodium hypochlorite solution (about 15% of active chlorine) and 6 ml of 10% strength sodium hydroxide solution is added dropwise to a solution of 1.5 g 2-[(4-methoxy-2-pyridyl)methylthio]-5-(1,1,2,2-tetrafluoroethoxy)-1H-benzimidazole in 30 ml of ethyl acetate at 0° C. in the course of 20 min., stirring is continued at this temperature for 20 min. and 0.6 ml of 10% strength sodium thiosulfate solution is then added. 1.5 g of ammonium sulfate are added and the organic phase is separated off, washed with saturated sodium chloride solution, dried with magnesium sulfate and concentrated to a small volume. 1.3 g (85%) of the title compound of melting point 131°–132° C. (decomposition) are obtained by precipitation with diisopropyl ether.

3.

2-[(4-Methoxy-2-pyridyl)methylthio]-5-trifluoromethoxy-1H-benzimidazole 4.0 g of 2-mercapto-5-trifluoromethoxy-1H-benzimidazole and 3.5 g of 2-chloromethyl-4-methoxypyridine hydrochloride are heated at the boiling point in 100 ml of isopropanol for 4.5 h, under nitrogen. The mixture is cooled in an ice-bath and 7.0 g (96%) of the dihydrochloride of the title compound of m.p. 164°–165° C. (decomposition) are obtained. The salt is dissolved in water, the solution is clarified with active charcoal and the base is liberated with potassium bicarbonate solution. The mixture is extracted with methylene chloride and the organic solution is dried with magnesium sulfate and concentrated in vacuo. The residue is crystallized from cyclohexane. 5.2 g (86%) of the title compound of m.p. 134°–135° C. are obtained.

The following compounds are obtained analogously:

2-[(4-methoxy-3-methyl-2-pyridyl)methylthio]-5-trifluoromethoxy-1H-benzimidazole of m.p. 180°–181° C. (from cyclohexane) and 2-[(4-methoxy-5-methyl-2-pyridyl)methylthio]-5-trifluoromethoxy-1H-benzimidazole of m.p. 148°–149° C. (from water)

by reacting 2-mercapto-5-trifluoromethoxy-1H-benzimidazole with 2-chloromethyl-4-methoxy-3-methylpyridine hydrochloride and 2-chloromethyl-4-methoxy-5-methylpyridine hydrochloride.

The following compounds are obtained analogously:

2-[(4-methoxy-2-pyridyl)methylthio]-5-(1,1,2,2-tetrafluoroethoxy)-1H-benzimidazole of m.p. 130°–131° C. (from isopropanol).

2-[(4-methoxy-3-methyl-2-pyridyl)methylthio]-5-(1,1,2,2-tetrafluoroethoxy)-1H-benzimidazole of m.p. 110°–111° C. (from isopropanol), 2-[(4-methoxy-5-methyl-2-pyridyl)methylthio]-5-(1,1,2,2-tetrafluoroethoxy)-1H-benzimidazole of m.p. 135°–136° C. (from isopropanol) and 2-[(3-methyl-2-pyridyl)methylthio]-5-(1,1,2,2-tetrafluoroethoxy)-1H-benzimidazole of m.p. 129°–130° C. (from isopropanol)

by reacting 2-mercapto-5-(1,1,2,2-tetrafluoroethoxy)-1H-benzimidazole with the hydrochlorides of 2-chloromethyl-4-methoxypyridine, 2-chloromethyl-4-methoxy-3-methylpyridine, 2-chloromethyl-4-methoxy-5-methylpyridine and 2-chloromethyl-3-methylpyridine in isopropanol.

The following compounds are obtained analogously:

2-[(4-methoxy-2-pyridyl)methylthio]-5-(2,2,2-trifluoroethoxy)-1H-benzimidazole of m.p. 134°–135° C. (from toluene), 2-[(4-methoxy-3-methyl-2-pyridyl)methylthio]-5-(2,2,2-trifluoroethoxy)-1H-benzimidazole of m.p. 178°–179° C. (from toluene), 5-chlorodifluoromethoxy-2-[(4-methoxy-2-pyridyl)methylthio]-1H-benzimidazole of m.p. 135°–137° C. (from toluene), 5-chlorodifluoromethoxy-2-[(4-methoxy-3-methyl-2-pyridyl)methylthio]-1H-benzimidazole of m.p. 171°–173° C. (from toluene), 5-difluoromethoxy-2-[(4-methoxy-2-pyridyl)methylthio]-1H-benzimidazole of m.p. 115°–117° C. (from toluene), 5-difluoromethoxy-2-[(4-methoxy-3-methyl-2-pyridyl)methylthio]-1H-benzimidazole of m.p. 167°–169° C. (from toluene), 5,6-bis(difluoromethoxy)-2-[(4-methoxy-2-pyridyl)methylthio]-1H-benzimidazol of m.p. 132°–134° C. (from toluene), 5,6-bis(difluoromethoxy)-2-[(4-methoxy-3-methyl-2-pyridyl)methylthio]-1H-benzimidazole of m.p. 163°–165° C. (from toluene), 5-difluoromethoxy-6-fluoro-2-[(4-methoxy-2-pyridyl)methylthio]-1H-benzimidazole of m.p. 140°–142° C. (from toluene), 5-difluoromethoxy-6-methoxy-2-[(4-methoxy-2-pyridyl)methylthio]-1H-benzimidazole of m.p. 124°–125° C. (from toluene), 5-difluoromethoxy-6-methoxy-2-[(4-methoxy-3-methyl-2-pyridyl)methylthio]-1H-benzimidazole of m.p. 198°–191° C. (from toluene)

by reacting 2-mercapto-5-(2,2,2-trifluoroethoxy)-1H-benzimidazole, 5-chlorodifluoromethoxy-2-mercapto-1H-benzimidazole, 5-difluoromethoxy-2-mercapto-1H-benzimidazole, 5,6-bis(difluoromethoxy)-2-mercapto-1H-benzimidazole, 5-difluoromethoxy-6-fluoro-2-mercapto-1H-benzimidazole and 5-difluoromethoxy-2-mercapto-6-methoxy-1H-benzimidazole with 2-chloromethyl-4-methoxypyridine and 2-chloromethyl-4-methoxy-3-methylpyridine.

4.

2-[(4-Methoxy-3,5-dimethyl-2-pyridyl)methylthio]-5-trifluoromethoxy-1H-benzimidazole 5 ml of 4M sodium hydroxide solution are added dropwise to a mixture of 2.34 g of 2-mercapto-5-trifluromethoxy-1H-benzimidazole and 2.2 g of 2-chloromethyl-4-methoxy-3,5-dimethylpyridine hydrochloride in 50 ml of ethanol at room temperature and the mixture is stirred overnight at room temperature. The solvent is distilled off in vacuo, water is added, the mixture is extracted with ethyl acetate, the solution is dried and 4.3 g (95%) of the dihydrochloride of the title compound are precipitated with 4M hydrogen chloride in ether. The salt is dissolved in water and the base is precipitated with dilute sodium carbonate solution at pH 8 and recrystallized from diisopropyl ether. 3.0 g (78%) of the title compound of m.p. 152°–154° C. are obtained.

The following compound is obtained analogously:

2-[(4-methoxy-3,5-dimethyl-2-pyridyl)methylthio]-5-(1,1,2,2-tetrafluoroethoxy)-1H-benzimidazole (m.p. 120°–122° C.)

by reacting 2-mercapto-5-(1,1,2,2-tetrafluoroethoxy)-1H-benzimidazole with 2-chloromethyl-4-methoxy-3,5-dimethylpyridine hydrochloride.

5.

2-Mercapto-5-(1,1,2,2-tetrafluoroethoxy)-1H-benzimidazole (a) 55 g of 1-nitro-4-(1,1,2,2-tetrafluoroethoxy)benzene are hydrogenated in 300 ml of ethanol on 0.5 g of 10% strength palladium-on-charcoal in a circulatory hydrogenation apparatus under atmospheric pressure at 20°–45° C. for 1 h, the catalyst is filtered off and the solution is concentrated at 40° C. in vacuo. The 4-(1,1,2,2-tetrafluoroethoxy)aniline is diluted with 100 ml of glacial acetic acid, 23 ml of acetic anhydride are added dropwise at room temperature, 2 ml of water are added after 30 min., the solution is concentrated in vacuo at 50° C. after a short time and 500 ml of ice-water are added. 56 g (97%) of N-[4-(1,1,2,2-tetrafluoroethoxy)phenyl]-acetamide of m.p. 121°–122° C. are obtained.

(b) 55 g of the last-noted compound are dissolved in 380 ml of methylene chloride, 55 ml of 100% strength nitric acid are added dropwise at room temperature in the course of 10 min. and stirring is continued for 6 h. The organic solution is then washed with aqueous sodium carbonate solution and water, dried with magnesium sulfate and concentrated. 65 g (100%) of N-[2-nitro-4-(1,1,2,2-tetrafluoroethoxy)phenol]-acetamide of m.p. 80°–81° C. (from cyclohexane) are obtained.

(c) 63 g of the last-noted compound are dissolved in 450 ml of methanol. 106 ml of 6M sodium hydroxide solution are added dropwise at room temperature, the mixture is cooled in an ice-bath and 53 g (98%) of 2-nitro-4-(1,1,2,2-tetrafluoroethoxy)-aniline (m.p. 85°–86° C.) are precipitated by dropwise addition of 900 ml of water.

(d) 33 g of the last-noted compound are hydrogenated in about 600 ml of isopropanol on 1 g of 10% strength palladium-on-charcoal in a circulatory hydrogenation apparatus under atmospheric pressure and at room temperature. The catalyst is filtered off with suction and 34 g (89%) of 4-(1,1,2,2-tetrafluoroethoxy)-1,2-phenylenediamine dihydrochloride of m.p. 275°–276° C. (decomposition) are precipitated with 4M hydrogen chloride in ether.

(e) 330 ml of ethanol, 60 ml of water, 8.9 g of sodium hydroxide and 23 g of potassium 0-ethyldithiocarbonate (recrystallized from isopropanol) are added to 33 g of the compound obtained from step (d) and the mixture is heated at the boiling point under reflux for 15 h. 1.2 liters of icewater are added, the pH is brought to 13–14 with sodium hydroxide solution, the mixture is clarified with active charcoal and the product is precipitated with dilute hydrochloric acid up to pH 3.5. 27 g (91%) of the title compound of m.p. 316°–319° C. (from isopropanol) are obtained.

6. 2-Mercapto-5-trifluoromethoxy-1H-benzimidazole

The title compound of m.p. 305°–307° C. (decomposition, from toluene) is obtained in 75% yield analogously to Example 5e) by reacting 4-trifluoromethoxy-1,2-phenylenediamine dihydrochloride (compare C.A. 55, 23408d, 1961) with potassium 0-ethyldithiocarbonate and sodium hydroxide solution in ethanol.

7. 2-Mercapto-5-(2,2,2-trifluoroethoxy)-1H-benzimidazole (a) 50 g of 1-(2,2,2-trifluoroethoxy)-4-nitrobenzene (Synthesis 1980, page 727) are hydrogenated and acetylated analogously to Example 5a. 50 g (95%) of N-[4-(2,2,2-trifluoroethoxy)-phenyl]-acetamide of m.p. 140°–141° C. are obtained.

(b) 42 g of the above compound are stirred with 9.7 ml of 100% strength nitric acid in 290 ml of glacial acetic acid at room temperature for 18 h, and the product is precipitated with water. 47 g (94%) of N-[2-nitro-4-(2,2,2-trifluoroethoxy)-phenyl]-acetamide of m.p. 117°–118° C. are obtained.

(c) 47 g of the above compound are hydrolysed analogously to Example 5c, and 38.7 g (97%) of 2-nitro-4-(2,2,2-trifluoroethoxy)-aniline (m.p. 84°–85° C.) are obtained.

(d) 37 g of the above compound are hydrogenated analogously to Example 5d, and 41 g (94%) of 4-(2,2,2-trifluoroethoxy)-1,2-phenylenediamine dihydrochloride of m.p. 230°–233° C. (decomposition) are obtained.

(e) 36 g of the above compound are reacted analogously to Example 5e to give 30 g (94%) of the title compound of m.p. 288°–290° C.

8. 5-Chlorodifluoromethoxy-2-mercapto-1H-benzimidazole (a) 10.0 g of N-[4-(chlorodifluoromethoxy)phenyl]-acetamide (m.p. 101°–103° C., obtained from 4-chlorodifluoromethoxyaniline and acetic anhydride) and 12.3 ml of 100% strength nitric acid are stirred at 20° C. for 4 h in 80 ml of methylene chloride. The solution is neutralized with aqueous potassium bicarbonate solution, the organic phase is concentrated and 11.4 g (96%) of N-(4-chlorodifluoromethoxy-2-nitrophenyl)-acetamide of m.p. 89°–91° C. are obtained.

(b) 8.6 ml of a 30% strength solution of sodium methylate in methanol are added dropwise at 5° C. to a solution of 10.5 g of the above compound in 200 ml of methanol, stirring is continued for 2 h without cooling, ice-water is added, the pH is brought to 8 and 8.7 g (97%) of 4-chlorodifluoromethoxy-2-nitroaniline of m.p. 40°–42° C. are obtained.

(c) 8.5 g of the above compound are hydrogenated in 200 ml of methanol on 0.8 g of 10% strength palladium-on-charcoal under atmospheric pressure, and concentrated hydrochloric acid is added. The solution is filtered, concentrated and stirred with diisopropyl ether. 8.5 g (97%) of 4-chlorodifluoromethoxy-1,2-phenylenediamine dihydrochloride are obtained.

(d) 6.3 g (72%) of the title compound of m.p. 268°–270° C. (decomposition) are obtained from 8.5 g of the above compound ananlogously to Example 5e).

9. 5-Difluoromethoxy-2-mercapto-1H-benzimidazole (a) 11.8 g of N-(4-difluoromethoxyphenyl)-acetamide [L. M. Jagupol'skii et al., J. General Chemistry (USSR) 39, 190 (1969)] dissolved in 200 ml of methylene chloride are stirred with 12.1 ml of 100% strength hydrochloric acid for 1.5 h at room temperature. Analogously to Example 5b 13.3 g (92%) of N-[(4-difluoroethoxy-2-nitro)phenyl]-acetamide of m.p. 71°–73° C. are obtained.

(b) Analogously to Example 8b, 4-difluoromethoxy-2-nitroaniline of m.p. 68°–70° C. is obtained in 96% yield.

(c) Analogously to Example 8c, 4-difluoromethoxy-1,2-phenylenediamine dihydrochloride is obtained in 94% yield.

(d) Analogously to Example 5e, the title compound of m.p. 250°–252° C. (from isopropanol) is obtained in 78% yield.

10. 5,6-Bis(difluoromethoxy)-2-mercapto-1H-benzimidazole (a) Analogously to L. N. Sedova et al., Zh. Org. Khim. 6, 568 (1970), 275 g of chlorodifluoromethane are passed into a solution of 100 g of o-dihydroxy-benzene, 220 g of sodium hydroxide and 60 g of sodium dithionite in 500 ml of water and 400 ml of dioxane at 50°–55° C. After distillation at 61°–62° C./1.0–1.1 kPa a mixture of 1,2-bis(difluoromethoxy)benzene and 2-difluoroethoxyphenol is obtained, which is separated by chromatography on silica gel with cyclohexane/ethyl acetate (4:1).

(b) A solution of 15 g of 1,2-bis(difluoromethoxy)benzene and 15 ml of 100% strength nitric acid in 150 ml of methylene chloride is stirred for 7 h at room temperature. The solution is neutralized with potassium bicarbonate solution and the organic phase is separated off. After chromatography on silica gel with cyclohexane/ethyl acetate (4:1), 1,2-bis(difluoromethoxy)-4-nitrobenzene is obtained, which is hydrogenated and acetylated analogously to Example 5a to yield N-[3,4-bis(difluoromethoxy)phenyl]-acetamide of m.p. 81°–83° C. Further reaction analogously to Example 5 gives N-[4,5-bis(difluoromethoxy)-2-nitrophenyl]-acetamide of m.p. 65°–67° C., N-[4,5-bis(difluoromethoxy)-2-nitro]-aniline of m.p. 107°–109° C., 4,5-bis(difluoromethoxy)-1,2-phenylenediamine dihydrochloride and the title compound of m.p. 285°–287° C. (decomposition; from isopropanol).

11.
5-Difluoromethoxy-2-mercapto-6-methoxy-1H-benzimidazole (a) 58 g of chlorodifluoromethane are passed into a solution of 55.5 g of guaiacol and 130 g of sodium hydroxide in 300 ml of water and 300 ml of dioxane at 60° C. The mixture is filtered at 10° C. and the organic phase is separated off, dried with anhydrous potassium carbonate and distilled. 56 g (73%) of 1-difluoromethoxy-2-methoxybenzene of boiling point 75°–79° C./0.9 kPa are obtained.

(b) A solution of 33.8 ml of 100% strength nitric acid in 90 ml of methylene chloride is added dropwise at 0°–5° C. to a solution of 47 g of the above compound in 230 ml of methylene chloride. After 30 min., 250 ml of ice-water are added, and the mixture is neutralized with potassium bicarbonate. The dried organic phase is concentrated in vacuo, and the residue is recrystallized from cyclohexane. 53 g (90%) of 1-difluoromethoxy-2-methoxy-5-nitrobenzene (m.p. 48°–49° C.) are obtained, which are hydrogenated and acetylated analogously to Example 5a. N-(3-difluoromethoxy-4-methoxyphenyl)-acetamide of m.p. 129°–130° C. are obtained in 90% yield.

(c) 46 g of the above compound are nitrated with 33 ml of 100% strength nitric acid in methylene chloride analogously to the above procedure. N-(5-difluoromethoxy-4-methoxy)-2-nitrophenyl)-acetamide of m.p. 116°–117° C. are obtained in 99% yield.

(d) 54 g of the above compound in 810 ml of methanol are stirred for 1 h at room temperature with 44.8 ml of a 30% strength solution of sodium methylate in methanol. The mixture is concentrated in vacuo, ice-water and glacial acetic acid are added up to pH 8, and 5-difluoromethoxy-4-methoxy-2-nitroaniline of m.p. 144°–145° C. is obtained in 99% yield.

(e) 25 g of the above compound in 300 ml of methanol are hydrogenated on 1.25 g of 10% strength palladium-on-charcoal analogously to Example 5d. 26 g (88%) of 3-difluoromethoxy-4-methoxy-1,2-phenylenediamine dihydrochloride of m.p. 218°–220° C. (decomposition) are obtained.

(f) 25 g of the above compound are reacted with 19 g of potassium-0-ethyldithiocarbonate analogously to Example 5e. 20 g of (89%) of the title compound of m.p. 280°–282° C. (decomposition; from isopropanol) are obtained.

12.
5-Difluoromethoxy-6-fluoro-2-mercapto-1H-benzimidazole (a) Analogously to Example 11a, 1-difluoromethoxy-2-fluorobenzene (boiling point 86° C./10 kPa; $n_D^{20}=1.4340$) is obtained from 2-fluorophenol and chlorodifluoromethane.

(b) 38.4 ml of 100% strength nitric acid are added dropwise with stirring at −10° C. to 30 g of the above compound in 300 ml of methylene chloride, and stirring is continued for 1 h at −10° C. and 2.5 h at 0° C. After addition of ice-water, neutralization and chromatography on silica gel with ethyl acetate/cyclohexane (4:1), 34 g of an oil are obtained, consisting of 90% of 1-difluoromethoxy-2-fluoro-4-nitrobenzene and 10% of 1-difluoromethoxy-2-fluoro-5-nitrobenzene (NMR-spectrum).

(c) 30 g of the above mixture are hydrogenated and acetylated analogously to Example 5a. After recrystallization from toluene, 21 g (65%) of N-(4-difluoromethoxy-3-fluorophenyl)-acetamide of m.p. 112°–113° C. are obtained.

(d) 22.5 ml of 100% strength nitric acid are added dropwise to 20 g of the above compound in 200 ml of methylene chloride at 20° C. in the course of 30 min., and stirring is continued for 15 h at room temperature. Analogously to Examples 11c, N-(4-difluoroethoxy-5-fluoro-2-nitrophenyl)-acetamide of m.p. 72°–74° C. (89% yield, from cyclohexane), is obtained. Stirring this compound for several hours with 1M hydrogen chloride in methanol at 60° C. yields 4-difluoromethoxy-5-fluoro-2-nitroaniline of m.p. 95°–97,5° C. (95% yield), and further reaction analogously to Example 11e gives 4-difluoromethoxy-5-fluoro-1,2-phenylenediamine dihydrochloride (85% yield, decomposition at 210° C.)

(e) 15 g of the above compound are reacted analogously to Example 5e with 11.8 g of potassium 0-ethyldithiocarbonate. 11.1 g (84%) of the title compound of m.p. 275°–276° C. (from isopropanol) are obtained.

13.
2-[(4-Methoxy-2-pyridyl)methylsulfinyl]-5-(1,1,2,2-tetrafluoroethoxy)-1H-benzimidazole sodium salt 50 ml of 0.1M sodium hydroxide solution and 50 ml of aceton are added to 2.017 g of 2-[(4-methoxy-2-pyridyl)-methylsulfinyl]-5-(1,1,2,2-tetrafluoroethoxy)-1H-benzimidazole. The resulting solution is concentrated on a rotatory evaporator at 60° C., and the residue is crystallized from ether. After drying at 60° C. in vacuo over calcium chloride the title compound is obtained as hydrate.

The following compounds are obtained analogously:
2-[(4-methoxy-2-pyridyl)methylsulfinyl]-5-trifluoromethoxy-1H-benzimidazole sodium salt,
2-[(4-methoxy-3-methyl-2-pyridyl)methylsulfinyl]-5-trifluoromethoxy-1H-benzimidazole sodium salt and
5-difluoromethoxy-6-methoxy-2-[(4-methoxy-3-methyl-2-pyridyl)methylsulfinyl]-1H-benzimidazole sodium salt.

14. 2-Chloromethyl-4-methoxypyridine hydrochloride 15 ml of thionyl chloride are added dropwise to a solution, cooled to −10° C., of 10 g (0.072 mole) of 2-hydroxymethyl-4-methoxypyridine in 30 ml of dry chloroform in the course of 15 min.. The solution is allowed to come to room temperature and stirring is continued for 1.5 h. After the solvent and the eccess thionyl chloride have been stripped off, colorless crystals are obtained, and these are recrystallized from isopropanol [12.1 g (87%), m.p. 149°–150° C., decomposition].

Analogously, reaction of
2-hydroxymethyl-4-methoxy-3-methylpyridine,
2-hydroxymethyl-4-methoxy-3,5-dimethylpyridine,
2-hydroxymethyl-4methoxy-5-methylpyridine and
2-hydroxymethyl-3-methylpyridine with thionyl chloride
gives
2-chloromethyl-4-methoxy-3-methylpyridine hydrochloride (m.p. 157°–158° C., decomposition, from isopropanol/ether), 2-chloromethyl-4-methoxy-3,5-dimethylpyridine hydrochloride [m.p. 135°-136° C. (decomposition) from isopropanol ether].
2-chloromethyl-4-methoxy-5-methylpyridine hydrochloride (m.p. 147° C., decomposition) and
2-chloromethyl-3-methylpyridine hydrochloride (m.p. 163°-165° C.).

The hydroxy-pyridines (see also Example 15) are obtained in accordance with the method of or the instructions of O. E. Schulz and S. Fedders. Arch. Pharm. (Weinheim) 310, 128 (1977). The appropriately required intermediates are prepared in accordance with the method of H. C. Brown, S. Johnson and H. Podall, J.Am.Chem.Soc. 76, 5556 (1954).

15. 2-Hydroxymethyl-4-methoxy-3,5-dimethylpyridine hydrochloride 18 g of 2,3,5-trimethylpyridine [F. Bohlmann, A. Englisch, J. Politt, H. Sander and W. Weise, Chem. Ber. 88 (1955)] and 17 ml of 30% strength hydrogen peroxide are warmed at 100° C. in 80 ml of glacial acetic acid for 2.5 h. A further 10 ml of 30% strength hydrogen peroxide are then added and the temperature is maintained for a further 8 h. The mixture is subsequently concentrated to half the volume under a waterpump vacuum and is subjected to a peroxide test. When free from peroxide, all the solvent is stripped off in vacuo and the residue is distilled under a high vacuum. 19.2 g (95%) of 2,3,5-trimethylpyridine N-oxide pass over at 95°-98° C. under 0.01 mm Hg (1.33 Pa).

5.0 g of this product are dissolved in a mixture of 7 ml of fuming nitric acid and 7 ml of concentrated sulfuric acid at room temperature and the solution is warmed at a bath temperature of 40° C. for 18 h. Thereafter, it is poured onto ice-water and rendered alkaline with concentrated sodium hydroxide solution, with cooling. Extraction of the mixture with ethyl acetate and removal of the solvent in vacuo gives crude 2,3,5-trimethyl-4-nitropyridine N-oxide, which is dissolved in 20 ml of dry methanol without further purification. 4.7 ml of commercially available 30% strength sodium methoxide in methanol are added to this solution and the mixture is warmed at 50° C. for 12 h. Thereafter, the solvent is stripped off; the residue is taken up in a little water and the mixture is extracted with ethyl acetate. After the solvent has been stripped off, the crude 4-methoxy-2,3,4-trimethylpyridine N-oxide which remains as an oil, is poured, without further purification, into 20 ml of hot acetic anhydride at 100° C. and is warmed at this temperature for 1 h. Thereafter, the mixture is concentrated in vacuo, the residue is taken up, without further purification, in 20 ml of 10% strength aqueous hydrochloric acid and the mixture is stirred at 50° C. for 2.5 h. It is concentrated to half the volume is vacuo, rendered alkaline with potassium carbonate and extracted with ethyl acetate. The combined extracts are dried over sodium sulfate; the solvent is stripped off in vacuo. The oily residue is dissolved in 50 ml of ethyl methyl ketone, and ethereal hydrochloric acid is added until precipitation is quantitative. The precipitate is recrystallized from dioxane with a little isopropanol. 3.1 g of the title compound of m.p. 126° C. are obtained. After chromatography of the free base on a silica gel column, an m.p. of 49°-51° C. is found for the free base and, after reprecipitation in hydrogen chloride/ether, an m.p. of 133.5° C. (decomposition) is found for the hydrochloride.

2-Hydroxymethyl-4-methoxy-5-methylpyridine (m.p. 102°-104° C.) is obtained in a similar manner.

COMMERCIAL USEFULNESS

The fluoroalkoxy compounds of formula I and their salts have useful pharmacological properties which render them commercially useful. They significantly inhibit the secretion of gastric acid in warm-blooded animals and moreover have an excellent protective effect on the stomach and intestines in warm-blooded animals. This protective effect on the stomach and intestine is already observed when doses below the acid secretion-inhibiting doses are administered. Furthermore the compounds according to the invention are characterized by an absence of significant side-effects and an advantageous therapeutic range.

In this context, "protection of the stomach and intestines" means the prevention and treatment of gastrointestinal diseases, in particular gastrointestinal inflammatory diseases and lesions (such as, gastric ulcer, duodenal ulcer, gastritis, hyperacid stomach irritation or stomach irritation caused by medicaments), which can be caused, for example, by microorganisms, bacterial toxins, medicaments (for example certain antiphlogistics and antirheumatics), chemicals (for example ethanol), gastric acid or stress situations.

A further advantage of the compounds according to the invention is their comparatively high chemical stability.

Surprisingly, the excellent properties of the compounds according to the invention prove to be significantly superior to those of the compounds known for the prior art. On the basis of these properties, the fluoroalkoxy compounds and their pharmacologically-acceptable salts are outstandingly suitable for use in human and veterinary medicine, and they are particularly used for the treatment and prophylaxis of diseases of the stomach and intestines and those diseases based on excessive secretion of gastric acid.

The invention thus furthermore relates to the compounds according to the invention for use in the treatment and prophylaxis of the mentioned diseases.

The invention also relates to the use of the compounds according to the invention in the preparation of medicaments which are used for the treatment and prophylaxis of the mentioned diseases.

The invention furthermore relates to medicaments which contain one or more fluoroalkoxy compounds of formula I and/or their pharmacologically-acceptable salts.

The medicaments are prepared by processes which are known per se and with which the expert is familiar. As medicaments, the pharmacologically-active compounds (=active substances) according to the invention are used either as such or, preferably, in combination with suitable pharmaceutical auxiliaries, in the form of tablets, coated tablets, capsules, suppositories, emulsions, suspensions or solutions, the content of active substance advantageously being between 0.1 and 95%.

The expert is familiar with the auxiliaries which are suitable for the desired medicament formulations, on the basis of his expert knowledge. Besides solvents, gel-forming agents, suppository bases, tablet auxiliaries and other active-substance carriers, optional components include for example, antioxidants, dispersing agents, emulsifiers, anti-foaming agents, flavor-correcting agents, preservatives, solubilizing agents, colorants and, in particular, percutaneaous absorption promotors and complexing agents (e.g. cyclodextrins).

The active substances can be administered orally, parenterally or percutaneously.

In general, it has proved advantageous in human medicine to administer the active compound or compounds, in the case of oral administration, in a daily dose of from about 0.01 to about 20, preferably from 0.05 to 5 and in particular from 0.1 to 1.5 mg/kg of body weight, if necessary in the form of several, preferably 1 to 4, individual doses, in order to achieve the desired result. Similar or (especially in the case of intravenous administration of the active substances) as a rule lower dosages can be used for parenteral treatment. The particular optimum dosage required and the mode of administration of the active substances is easily determined by any expert on the basis of his expert knowledge.

When the compounds according to the invention and/or their salts are used for the treatment of the mentioned diseases, the pharmaceutical formulations contain one or more pharmacologically active constituents from other groups of medicaments, such as antacids, for example aluminum hydroxide and magnesium aluminate; tranquilizers, such as benzodiazepines, for example diazepam; spasmolytic agents, such as bietamiverine and camylofin; anticholinergic agents, such as oxyphencyclimine and phencarbamide; local anesthetics, such as tetracaine and procaine; and, when appropriate, also enzymes, vitamines or aminoacids.

The active substances are formulated, for example, in the following manner:

(a) Tablets containing 40 mg of active substance 20 kg of 2-[(4-methoxy-3-methyl-2-pyridyl)-methylthio]-5-trifluoromethoxy-1H-benzimidazole, 40 kg of lactose, 26 kg of maize starch and 3 kg of polyvinylpyrrolidone are moistened with about 210 liters of water and the mixture is granulated through a sieve of 1.25 mm mesh width. The granules are dried in a fluidized bed drier to a relative moisture of 50–60%, and 8 kg of sodium carboxymethylcellulose, 2 kg of talc and 1 kg of magnesium stearate are then added. The finished granules are pressed to tablets weighing 200 mg and having 8 mm in diameter.

(b) Capsules containing 30 mg of active substance 300 g of 2-[(4-methoxy-3-methyl-2-pyridyl)-methylsulfinyl]-5-trifluoromethoxy-1H-benzimidazole, 695 g of microcrystalline cellulose and 5 g of amorphous silicic acid are finely powdered and mixed thoroughly and size 4 hard gelatin capsules are filled with the mixture.

(c) Capsules containing 10 mg of active substance 100 g of 2-[(4-methoxy-3-methyl-2-pyridyl)-methylsulfinyl]-5-(1,1,2,2-tetrafluoroethoxy-1H-benzimidazole, 895 g of microcrystalline cellulose and 5 g of amorphous silicic acid are finely powdered and mixed thoroughly and size 4 hard gelatin capsules are filled with the mixture.

(d) Ampoules containing 10 mg of active substance 3,16 g of 2-[(4-methoxy-2-pyridyl)methylsulfinyl]-5-trifluoromethoxy-1H-benzimidazole sodium salt is dissolved in a solution of 0.5 g of sodium carbonate and 165,5 g of mannit in 1300 ml of distilled water, with stirring. The resulting solution is made up to 1500 ml with distilled water and sterile-filtered. In each case 5 ml of this solution are metered into a 15 ml vial and lyophilized. The lyophilizate can be reconstituted with 10 ml of water.

PHARMACOLOGY

The excellent protective effect on the stomach and the gastric secretion-inhibiting action of the fluoroalkoxy compounds according to the invention is demonstrated in animal experiments using the Shay rat model. In these experiments, the compounds according to the invention were compared with prior art compounds (A–D) of European Patent Applications Nos. 0 005 129 and 0 074 341. The compounds investigated are numbered as follows:

| Serial No. | Name of compound |
|---|---|
| A | 5-methoxy-2-[(4-methoxy-3,5-dimethyl-2-pyridylmethyl)thio]-1H—benzimidazole (EP 0 074 341) |
| B | 5-methoxy-2-[(4-methoxy-3,5-dimethyl-2-pyridylmethyl)sulfinyl]-1H—benzimidazole (EP 0 005 129) (INN: Omeprazole) |
| C | 5-methoxy-2-[(4-methoxy-5-methyl-2-pyridylmethyl)thio]-1H—benzimidazole (EP 0 074 341) |
| D | 5-methoxy-2-[(4-methoxy-5-methyl-2-pyridylmethyl)sulfinyl]-1H—benzimidazole (EP 0 005 129) |
| 1 | 2-[(4-methoxy-2-pyridyl)methylsulfinyl]-5-trifluoromethoxy-1H—benzimidazole |
| 2 | 2-[(4-methoxy-3-methyl-2-pyridyl)methylthio]-5-trifluoromethoxy-1H—benzimidazole |
| 3 | 2-[(4-methoxy-3-methyl-2-pyridyl)methylsulfinyl]-5-trifluoromethoxy-1H—benzimidazole |
| 4 | 2-[(4-methoxy-5-methyl-2-pyridyl)methylsulfinyl]-5-trifluoromethoxy-1H—benzimidazole |
| 5 | 2-[(4-methoxy-2-pyridyl)methylsulfinyl]-5-(1,1,2,2-tetrafluoroethoxy)-1H—benzimidazole |
| 6 | 2-[(4-methoxy-3-methyl-2-pyridyl)methylsulfinyl]-5-(1,1,2,2-tetrafluoroethoxy)-1H—benzimidazole |
| 7 | 2-[(4-methoxy-3-methyl-2-pyridyl)methylthio]-5-(1,1,2,2-tetrafluoroethoxy)-1H—benzimidazole |
| 8 | 2-[(4-methoxy-3,5-dimethyl-2-pyridyl)methylsulfinyl]-5-trifluoromethoxy-1H—benzimidazole |
| 9 | 2-[(4-methoxy-3,5-dimethyl-2-pyridyl)methylthio]-5-trifluoromethoxy-1H—benzimidazole |
| 10 | 2-[(4-methoxy-3-methyl-2-pyridyl)methylsulfinyl]-5-(2,2,2-trifluoroethoxy)-1H—benzimidazole |
| 11 | 2-[(4-methoxy-3-methyl-2-pyridyl)methylthio]-5-(2,2,2-trifluoroethoxy)-1H—benzimidazole |
| 12 | 5-difluoromethoxy-2-[(4-methoxy-3-methyl-2-pyridyl)methylsulfinyl]-1H—benzimidazole |
| 13 | 5,6-bis(difluoromethoxy)-2-[(4-methoxy-2-pyridyl)methylsulfinyl]-1H—benzimidazole |
| 14 | 5,6-bis(difluoromethoxy)-2-[(4-methoxy-3-methyl-2-pyridyl)methylsulfinyl]-1H—benzimidazole |
| 15 | 5,6-bis(difluoromethoxy)-2-[ (4-methoxy-3-methyl-2-pyridyl)methylthio]-1H—benzimidazole |
| 16 | 5-difluoromethoxy-6-methoxy-2-[(4-methoxy-3-methyl-2-pyridyl)methylsulfinyl]-1H—benzimidazole |
| 17 | 5-difluoromethoxy-6-methoxy-2-[(4-methoxy-3-methyl-2-pyridyl)methylthio]-1H—benzimidazole |
| 18 | 5-chlorodifluoromethoxy-2-[(4-methoxy-2-pyridyl)methylsulfinyl]-1H—benzimidazole |

The influence of the compounds of the prior art and the compounds according to the invention on gastric lesion formation induced by pyloric ligature (4 h; so-called Shay rat) and oral administration of 100 mg/kg of acetylsalicyclic acid, and the gastric secretion (HCl) in the course of 4 h in rats is shown in the following table.

| Protective effect on the stomach and inhibition of gastric secretion | | | | |
|---|---|---|---|---|
| | | Protective effect on the stomach (rats) Inhibition of | Gastric secretion (rats) | |
| Serial No. | n [Number of animals] | the lesion index, ED50* [mg/kg, perorally] | % inhibition of HCl secretion** | ED25* ED50* [mg/kg, perorally] |
| A | 88 | 9.0 | 20 | 12.0 25.0 |
| B | 112 | 2.2 | 29 | 1.9 4.6 |
| C | 24 | ~30.0 | | >60.6 |
| D | 40 | ~5.0 | 10 | 8.0 18.0 |
| 1 | 79 | 0.6 | 32 | 0.5 1.1 |
| 2 | 16 | 0.3 | 20 | 0.35 0.5 |
| 3 | 55 | 0.3 | 32 | <0.3 0.4 |
| 4 | 74 | 0.9 | 32 | 0.6 1.6 |
| 5 | 70 | 0.7 | 33 | 0.5 1.2 |
| 6 | 55 | 0.5 | 35 | 0.3 0.7 |
| 7 | 24 | 0.5 | 40 | 0.35 0.7 |
| 8 | 24 | 0.4 | 20 | 1.0 1.5 |
| 9 | 24 | 1.0 | 10 | 1.4 2.0 |
| 10 | 24 | 0.5 | 25 | 0.5 0.7 |
| 11 | 24 | 0.5 | 25 | 0.5 0.7 |
| 12 | 16 | ~0.3 | ~20 | ~0.3 ~0.6 |
| 13 | 16 | ~1.2 | ~30 | ~1.1 ~1.7 |
| 14 | 32 | 0.2 | 20 | ~0.3 0.6 |
| 15 | 32 | 0.6 | 30 | 0.5 1.0 |
| 16 | 32 | 0.2 | | ~0.8 |
| 17 | 32 | ~0.3 | ~25 | ~0.3 ~0.8 |
| 18 | 16 | 1.3 | 35 | <1.0 1.8 |

*ED25 and ED50 = dose which reduces the lesion index or the HCL secretion(4h) in the rat stomach by 25 and, respectively, 50% in the treated group in comparison with the control group.
**after administration of the antiulcerous ED50.

The antiulcerogenic action was tested by the so-called Shay rat method:

Ulcers are caused in rats which have been fasted for 24 hours (female, 180–200 g, 4 animals per cage on a high grid) by pyloric ligature (under diethyl ether anesthesia) and oral administration of 100 mg/10 ml/kg of acetylsalicylic acid. The substances to be tested are administered orally (10 ml/kg) one hour before the pyloric ligature. The wound is closed by means of Michel clamps. 4 hours thereafter, the animals are sacrificed under ether anesthesia by Atlas dislocation and resection of the stomach. The stomach is opened longitudinally and attached to a cork plate, after the amount of gastric juice secreted (volume) and later its HCl content (titration with sodium hydroxide solution) have first been determined; the number and size (=diameter) of the ulcers present are determined under a stereomicroscope at 10-fold magnification. The product of the degree of severity (according to the following points scale) and number of ulcers serves as the individual lesion index.

| Points scale: | |
|---|---|
| no ulcers | 0 |
| Ulcer diameter 0.1–1.4 mm | 1 |
| 1.5–2.4 mm | 2 |
| 2.5–3.4 mm | 3 |
| 3.5–4.4 mm | 4 |
| 4.5–5.4 mm | 5 |
| >5.5 mm | 6 |

The reduction in the average lesion index of each treated group compared with the control group (=100%) serves as a measure of the antiulcerogenic effect. The ED25 and ED50 designate those doses which reduce the average lesion index or the HCl secretion by 25% or, respectively, 50% in comparison with the control.

Toxicity

The LD50 of all the compounds tested is above 1,000 mg/kg [perorally] in mice.

What is claimed is:

1. A fluoroalkoxy compound of the formula

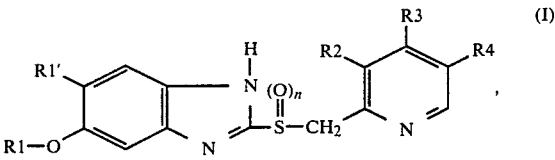

wherein

R1 represents a 1–3C-alkyl radical in the structure of which most or all hydrogen atoms are replaced by fluorine atoms, or a chlorodifluoromethyl radical, R1' represents hydrogen, halogen, trifluoromethyl, a 1–3C-alkyl radical, or a 1–3C-alkoxy radical in the structure of which optionally most or all hydrogen atoms are replaced by fluorine atoms, R2 represents hydrogen or a 1–3C-alkyl radical, R3 represents hydrogen or a 1–3C-alkyl or 1–3C-alkoxy radical, R4 represents hydrogen or a 1–3C-alkyl radical and n represents the number 0 or 1, or a salt thereof.

2. A compound according to claim 1, in which R1 represents a 1–3C-alkyl radical in the structure of which most or all hydrogen atoms are replaced by fluorine atoms, R1' represents hydrogen, halogen, trifluoromethyl or a 1–3C-alkoxy radical in the structure which most or all hydrogen atoms are replaced by fluorine atoms, and R2, R3, R4 and n have the meanings ascribed to them in claim 1, or a salt thereof.

3. A compound according to claim 1, in which R1 represents a 1–3C-alkyl radical in the structure of which most or all hydrogen atoms are replaced by fluorine atoms, and R1', R2, R3, R4 and n have the meanings ascribed to them in claim 1, or a salt thereof.

4. A compound according to claim 1, in which R1' represents hydrogen, halogen, trifluoromethyl, or a 1–3C-alkoxy radial in the structure which most or all hydrogen atoms are replaced by fluorine atoms, and R1, R2, R3, R4 and n have the meanings ascribed to them in claim 1, or a salt thereof.

5. A compound according to claim 1, in which R1 represents a trifluoromethyl, 1,1,2,2-tetrafluoroethyl, 2,2,2-trifluoroethyl, difluoromethyl or chlorodifluoromethyl radical, R1' represents hydrogen, fluorine, methoxy or difluoromethoxy, R2 represents hydrogen or methyl, R3 represents hydrogen or methoxy, R4 represents hydrogen or methyl and n represents the number 0 or 1, and wherein R2, R3 and R4 are not simultaneously hydrogen atoms, or a salt thereof.

6. A compound according to claim 1, in which R1 represents a trifluoromethyl, 1,1,2,2-tetrafluoroethyl, 2,2,2-trifluoroethyl, or difluoromethyl radical, R1' represents hydrogen, fluorine, or difluoromethoxy, R2 represents hydrogen or methyl, R3 represents hydrogen or methoxy, R4 represents hydrogen or methyl and n represents the number 0 or 1, and wherein R2, R3 and R4 are not simultaneously hydrogen atoms, or a salt thereof.

7. A compound according to claim 1, in which R1 represents a trifluoromethyl, 1,1,2,2-tetrafluoroethyl, 2,2,2-trifluoroethyl, or difluoromethyl radical, R1' represents hydrogen, fluorine, methoxy or difluoromethoxy, R2 represents hydrogen or methyl, R3 represents hydrogen or methoxy, R4 represents hydrogen or methyl and n represents the number 0 or 1, and wherein R2, R3 and R4 are not simultaneously hydrogen atoms, or a salt thereof.

8. A compound according to claim 1, in which R1 represents a trifluoromethyl, 1,1,2,2-tetrafluoroethyl, 2,2,2-trifluoroethyl, difluoromethyl, or chlorodifluoromethyl radical, R1' represents hydrogen, fluorine, or difluoromethoxy, R2 represents hydrogen or methyl, R3 represents hydrogen or methoxy, R4 represents hydrogen or methyl and n represents the number 0 or 1, and wherein R2, R3 and R4 are not simultaneously hydrogen atoms, or a salt thereof.

9. A compound according to claim 1, in which R1 represents a trifluoromethyl, 1,1,2,2-tetrafluoroethyl, 2,2,2-trifluoroethyl, difluoromethyl or chlorodifluoromethyl radical, R1' represents hydrogen, R2 represents hydrogen or methyl, R3 represents methoxy, R4 represents hydrogen or methyl and n represents the number 0 or 1, or a pharmacologically-acceptable salt thereof.

10. A compound according to claim 1, in which R1 represents a difluoromethyl radical, R1' represents fluorine, methoxy or difluoromethoxy, R2 represents hydrogen or methyl, R3 represents methoxy, R4 represents hydrogen or methyl and n represents the number 0 or 1, or a pharmacologically acceptable salt thereof.

11. A compound according to claim 1, in which R1 represents a trifluoroemthyl, 1,1,2,2-tetrafluoroethyl, 2,2,2-trifluoroethyl or difluoromethyl radical, R1' represents hydrogen, R2 represents hydrogen or methyl, R3 represents methoxy, R4 represents hydrogen or methyl and n represents the number 0 or 1, or a pharmacologically-acceptable salt thereof.

12. A compound according to claim 1, in which R1 represents a trifluoromethyl, 1,1,2,2-tetrafluoroethyl, 2,2,2-trifluoroethyl or difluoromethyl radical, R1' represents fluorine, methoxy or difluoromethoxy, R2 represents hydrogen or methyl, R3 represents methoxy, R4 represents hydrogen or methyl and n represents the number 0 or 1, or a pharmacologically-acceptable salt thereof.

13. A compound according to claim 1, in which R1 represents a trifluoromethyl, 1,1,2,2-tetrafluoroethyl, 2,2,2-trifluoroethyl, difluoromethyl or chlorodifluoromethyl radical, R1' represents hydrogen, R2 represents hydrogen or methyl, R3 represents methoxy, R4 represents hydrogen or methyl and n represents the number 0 or 1, or a pharmacologically-acceptable salt thereof.

14. A compound according to claim 1 in which n represents the number 0.

15. A compound according to claim 1 in which n represents the number 1.

16. A compound according to claim 1, selected from the group consisting of
2-[(4-Methoxy-2-pyridyl)methylsulfinyl]-5-trifluoromethoxy-1H-benzimidazole,
2-[(4-methoxy-3-methyl-2-pyridyl)methylthio]-5-trifluoromethoxy-1H-benzimidazole,
2-[(4-methoxy-3-methyl-2-pyridyl)methylsulfinyl]-5-trifluoromethoxy-1H-benzimidazole,
2-[(4-methoxy-5-methyl-2-pyridyl)methylsulfinyl]-5-trifluoromethoxy-1H-benzimidazole,
2-[(4-methoxy-2-pyridyl)methylsulfinyl]-5-(1,1,2,2-tetrafluoroethoxy)-1H-benzimidazole,
2-[(4-methoxy-3-methyl-2-pyridyl)methylsulfinyl]-5-(1,1,2,2-tetrafluoroethoxy)-1H-benzimidazole,
2-[(4-methoxy-3-methyl-2-pyridyl)methylthio]-5-(1,1,2,2-tetrafluoroethoxy)-1H-benzimidazole,
2-[(4-methoxy-3,5-dimethyl-2-pyridyl)methylsulfinyl]-5-trifluoromethoxy-1H-benzimidazole,
2-[(4-methoxy-3,5-dimethyl-2-pyridyl)methylthio]-5-trifluoromethoxy-1H-benzimidazole,
2-[(4-methoxy-3-methyl-2-pyridyl)methylsulfinyl]-5-(2,2,2-trifluoroethoxy)-1H-benzimidazole,
2-[(4-methoxy-3-methyl-2-pyridyl)methylthio]-5-(2,2,2-trifluoroethoxy)-1H-benzimidazole,
5-difluoromethoxy-2-[(4-methoxy-3-methyl-2-pyridyl)-methylsulfinyl]-1H-benzimidazole,
5,6-bis(difluoromethoxy)-2-[(4-methoxy-2-pyridyl)-methylsulfinyl]-1H-benzimidazole,
5,6-bis(difluoromethoxy)-2-[(4-methoxy-3-methyl-2-pyridyl)methylsulfinyl]-1H-benzimidazole,
5,6-bis(difluoromethoxy)-2-[(4-methoxy-3-methyl-2-pyridyl)methylthio]-1H-benzimidazole,
5-difluoromethoxy-6-methoxy-2-[(4-methoxy-3-methyl-2-pyridyl)methylsulfinyl]-1H-benzimidazole,
5-difluoromethoxy-6-methoxy-2-[(4-methoxy-3-methyl-2-pyridyl)methylthio]-1H-benzimidazole, and
5-chlorodifluoromethoxy-2-[(4-methoxy-2-pyridyl)-methylsulfinyl]-1H-benzimidazole;
or a pharmacologically-acceptable salt thereof.

17. A compound according to claim 10, in which R1' represents methoxy.

18. A compound according to claim 9, in which R1 represents trifluoromethyl.

19. A compound according to claim 9, in which R1 represents 1,1,2,2-tetrafluoroethyl.

20. A compound according to claim 9, in which R1 represents 2,2,2-trifluoroethyl.

21. A compound according to claim 9, in which R1 represents difluoromethyl.

22. A salt according to claim 1 which is a pharmacologically-acceptable salt.

23. The compound according to claim 1 which is 2-[(4-methoxy-2-pyridyl)methylsulfinyl]-5-(1,1,2,2-tetrafluoroethoxy)-1H-benzimidazole or a pharmacologically-acceptable salt thereof.

24. A medicament composition comprising a pharmaceutical auxilliary and from 0.1 to 95 percent by weight of a compound according to claim 1 or a pharmacologically-acceptable salt thereof.

25. A medicament composition, useful for treatment or prophylaxis of a gastrointestinal inflammatory disease and/or lesion which is caused, for example, by a microorganism, a bacterial toxin, a medicament, a chemical, gastric acid or stress, which comprises a pharmaceutical auxiliary and an effective amount of a compound according to claim 1 or of a pharmacologically-acceptable salt thereof.

26. A medicament composition for treatment or prophylaxis of a gastrointestinal inflammatory disease and/or lesion which is caused, for example, by a microorganism, a bacterial toxin, a medicament, a chemical, gastric acid or stress, and which comprises a pharmaceutical auxiliary and an effective amount of the compound of claim 23 or of a pharmacologically-acceptable salt thereof.

27. A method or treatment or prophylaxis of a gastro-intestinal inflammatory disease and/or lesion which is caused, for example, by a microorganism, a bacterial toxin, a medicament, a chemical, gastric acid or stress and which comprises administering an effective amount of a compound according to claim 1, or of a pharmaceutically-acceptable salt thereof, to a warm-blooded animal afflicted with or prone to an attack of such a disease.

28. A method or treatment or prophylaxis of a gastro-intestinal inflammatory disease and/or lesion which is caused, for example, by a microorganism, a bacterial toxin, a medicament, a chemical, gastric acid or stress and which comprises administering an effective amount of a composition according to claim 24 to a warm-blooded animal afflicted with or prone to an attack of such a disease.

29. A method of treatment or prophylaxis of a disease of the stomach and/or intestine based on excessive secretion of gastric acid and which comprises administering an effective amount of a compound according to claim 1, or of a pharmaceutically-acceptable salt thereof, to a warm-blooded animal afflicted with or prone to an attack of such a disease.

* * * * *